US007268214B2

(12) United States Patent
O'Mahony et al.

(10) Patent No.: US 7,268,214 B2
(45) Date of Patent: Sep. 11, 2007

(54) MEMBRANE TRANSLOCATING PEPTIDE DRUG DELIVERY SYSTEM

(75) Inventors: Daniel J. O'Mahony, Blackrock (IE); Imelda J. Lambkin, Sutton (IE)

(73) Assignee: Merrion Research I Limited, Dublin (IE)

( * ) Notice: Subject to any disclaimer, the term of this patent is extended or adjusted under 35 U.S.C. 154(b) by 1 day.

(21) Appl. No.: 10/764,235

(22) Filed: Jan. 23, 2004

(65) Prior Publication Data

US 2004/0138132 A1 Jul. 15, 2004

Related U.S. Application Data

(63) Continuation of application No. 09/671,089, filed on Sep. 27, 2000, now Pat. No. 6,780,846.

(60) Provisional application No. 60/156,246, filed on Sep. 27, 1999.

(51) Int. Cl.
*C07K 1/00* (2006.01)

(52) U.S. Cl. .................................................... 530/350

(58) Field of Classification Search ................ 530/350
See application file for complete search history.

(56) References Cited

U.S. PATENT DOCUMENTS 5,962,415 A * 10/1999 Nadler ........................ 514/12
6,248,558 B1 * 6/2001 Lin et al. .................. 435/69.1

* cited by examiner

*Primary Examiner*—Karen Cochrane Carlson
*Assistant Examiner*—Agnes Rooke
(74) *Attorney, Agent, or Firm*—Synnestvedt & Lechner LLP

(57) ABSTRACT

The present invention relates to a novel membrane translocating full-length peptide sequence, fragment, motif, derivative, analog or peptidomimetic thereof (MTLPs), to nucleotide sequences coding therefor, and to compositions comprising a MTLP-active agent complex and a MTLP-active particle complex. The MTLP or the nucleotide sequence coding therefor enhance movement of the active agent or of the active particle across a lipid membrane. More particularly, the present invention relates to a MTLP-active agent complex and a MTLP-active particle complex, wherein the MTLP enhances uptake of the active agent into a cell, into or out of an intracellular compartment and across a cell layer. Methods of making and methods of using MTLPs also are included.

13 Claims, 5 Drawing Sheets

Blood Glucose Levels Resulting from In vivo Delivery of Insulin by ZElan094-Insulin Nanoparticle Complexes and by Targeting Agent-Insulin Nanoparticle Complexes in the Rat Model $^3$H-fMLP Transport Across Caco-2 Monolayers in the Presence of ZElan094, 178, 187 and 022.

SEQUENCE LISTING

```
<160> NUMBER OF SEQ ID NOS: 59

<210> SEQ ID NO 1
<211> LENGTH: 12
<212> TYPE: PRT
<213> ORGANISM: Artificial Sequence
<220> FEATURE:
<223> OTHER INFORMATION: membrane translocating peptide

<400> SEQUENCE: 1

Ala Ala Val Leu Leu Pro Val Leu Leu Ala Ala Pro
1               5                   10


<210> SEQ ID NO 2
<211> LENGTH: 15
<212> TYPE: PRT
<213> ORGANISM: Artificial Sequence
<220> FEATURE:
```

-continued

```
<223> OTHER INFORMATION: membrane translocating peptide
<220> FEATURE:
<221> NAME/KEY: MOD_RES
<222> LOCATION: (15)..(15)
<223> OTHER INFORMATION: linked to FITC-LC

<400> SEQUENCE: 2

Lys Lys Ala Ala Ala Val Leu Leu Pro Val Leu Leu Ala Ala Pro
1               5                   10                  15


<210> SEQ ID NO 3
<211> LENGTH: 16
<212> TYPE: PRT
<213> ORGANISM: Artificial Sequence
<220> FEATURE:
<223> OTHER INFORMATION: membrane translocating peptide

<400> SEQUENCE: 3

Lys Lys Lys Ala Ala Ala Val Leu Leu Pro Val Leu Leu Ala Ala Pro
1               5                   10                  15


<210> SEQ ID NO 4
<211> LENGTH: 19
<212> TYPE: PRT
<213> ORGANISM: Artificial Sequence
<220> FEATURE:
<223> OTHER INFORMATION: membrane translocating peptide

<400> SEQUENCE: 4

Lys Lys Ala Ala Ala Val Leu Leu Pro Val Leu Leu Ala Ala Pro Arg
1               5                   10                  15

Glu Asp Leu


<210> SEQ ID NO 5
<211> LENGTH: 16
<212> TYPE: PRT
<213> ORGANISM: Artificial Sequence
<220> FEATURE:
<223> OTHER INFORMATION: membrane translocating peptide, cyclic

<400> SEQUENCE: 5

Lys Lys Cys Ala Ala Val Leu Leu Pro Val Leu Leu Ala Ala Pro Cys
1               5                   10                  15


<210> SEQ ID NO 6
<211> LENGTH: 13
<212> TYPE: PRT
<213> ORGANISM: Artificial Sequence
<220> FEATURE:
<223> OTHER INFORMATION: membrane translocating peptide, cyclic

<400> SEQUENCE: 6

Cys Ala Ala Val Leu Leu Pro Val Leu Leu Ala Ala Cys
1               5                   10


<210> SEQ ID NO 7
<211> LENGTH: 14
<212> TYPE: PRT
<213> ORGANISM: Artificial Sequence
<220> FEATURE:
<223> OTHER INFORMATION: membrane translocating peptide, cyclic internal

<400> SEQUENCE: 7

Lys Lys Cys Ala Ala Val Leu Leu Pro Val Leu Leu Ala Cys
1               5                   10
```

-continued

<210> SEQ ID NO 8
<211> LENGTH: 11
<212> TYPE: PRT
<213> ORGANISM: Artificial Sequence
<220> FEATURE:
<223> OTHER INFORMATION: membrane translocating peptide, cyclic

<400> SEQUENCE: 8

Cys Ala Ala Val Leu Leu Pro Val Leu Leu Cys
1 5 10

<210> SEQ ID NO 9
<211> LENGTH: 10
<212> TYPE: PRT
<213> ORGANISM: Artificial Sequence
<220> FEATURE:
<223> OTHER INFORMATION: membrane translocating peptide, cyclic

<400> SEQUENCE: 9

Cys Ala Ala Val Leu Leu Pro Val Leu Cys
1 5 10

<210> SEQ ID NO 10
<211> LENGTH: 13
<212> TYPE: PRT
<213> ORGANISM: Artificial Sequence
<220> FEATURE:
<223> OTHER INFORMATION: membrane translocating peptide, cyclic

<400> SEQUENCE: 10

Cys Ala Val Leu Leu Pro Val Leu Leu Ala Ala Pro Cys
1 5 10

<210> SEQ ID NO 11
<211> LENGTH: 12
<212> TYPE: PRT
<213> ORGANISM: Artificial Sequence
<220> FEATURE:
<223> OTHER INFORMATION: membrane translocating peptide, cyclic

<400> SEQUENCE: 11

Cys Val Leu Leu Pro Val Leu Leu Ala Ala Pro Cys
1 5 10

<210> SEQ ID NO 12
<211> LENGTH: 11
<212> TYPE: PRT
<213> ORGANISM: Artificial Sequence
<220> FEATURE:
<223> OTHER INFORMATION: membrane translocating peptide, cyclic

<400> SEQUENCE: 12

Cys Leu Leu Pro Val Leu Leu Ala Ala Pro Cys
1 5 10

<210> SEQ ID NO 13
<211> LENGTH: 10
<212> TYPE: PRT
<213> ORGANISM: Artificial Sequence
<220> FEATURE:
<223> OTHER INFORMATION: membrane translocating peptide, cyclic

<400> SEQUENCE: 13

Cys Leu Pro Val Leu Leu Ala Ala Pro Cys
1 5 10

<210> SEQ ID NO 14

-continued

<211> LENGTH: 12
<212> TYPE: PRT
<213> ORGANISM: Artificial Sequence
<220> FEATURE:
<223> OTHER INFORMATION: membrane translocating peptide

<400> SEQUENCE: 14

Ala Ala Val Leu Leu Pro Val Leu Leu Ala Ala Pro
1 5 10

<210> SEQ ID NO 15
<211> LENGTH: 11
<212> TYPE: PRT
<213> ORGANISM: Artificial Sequence
<220> FEATURE:
<223> OTHER INFORMATION: membrane translocating peptide

<400> SEQUENCE: 15

Ala Ala Val Leu Leu Pro Val Leu Leu Ala Ala
1 5 10

<210> SEQ ID NO 16
<211> LENGTH: 12
<212> TYPE: PRT
<213> ORGANISM: Artificial Sequence
<220> FEATURE:
<223> OTHER INFORMATION: membrane translocating peptide

<400> SEQUENCE: 16

Lys Lys Ala Ala Val Leu Leu Pro Val Leu Leu Ala
1 5 10

<210> SEQ ID NO 17
<211> LENGTH: 9
<212> TYPE: PRT
<213> ORGANISM: Artificial Sequence
<220> FEATURE:
<223> OTHER INFORMATION: membrane translocating peptide

<400> SEQUENCE: 17

Ala Ala Val Leu Leu Pro Val Leu Leu
1 5

<210> SEQ ID NO 18
<211> LENGTH: 8
<212> TYPE: PRT
<213> ORGANISM: Artificial Sequence
<220> FEATURE:
<223> OTHER INFORMATION: membrane translocating peptide

<400> SEQUENCE: 18

Ala Ala Val Leu Leu Pro Val Leu
1 5

<210> SEQ ID NO 19
<211> LENGTH: 11
<212> TYPE: PRT
<213> ORGANISM: Artificial Sequence
<220> FEATURE:
<223> OTHER INFORMATION: membrane translocating peptide

<400> SEQUENCE: 19

Ala Val Leu Leu Pro Val Leu Leu Ala Ala Pro
1 5 10

<210> SEQ ID NO 20
<211> LENGTH: 10

-continued

<212> TYPE: PRT
<213> ORGANISM: Artificial Sequence
<220> FEATURE:
<223> OTHER INFORMATION: membrane translocating peptide

<400> SEQUENCE: 20

Val Leu Leu Pro Val Leu Leu Ala Ala Pro
1 5 10

<210> SEQ ID NO 21
<211> LENGTH: 9
<212> TYPE: PRT
<213> ORGANISM: Artificial Sequence
<220> FEATURE:
<223> OTHER INFORMATION: membrane translocating peptide

<400> SEQUENCE: 21

Leu Leu Pro Val Leu Leu Ala Ala Pro
1 5

<210> SEQ ID NO 22
<211> LENGTH: 8
<212> TYPE: PRT
<213> ORGANISM: Artificial Sequence
<220> FEATURE:
<223> OTHER INFORMATION: membrane translocating peptide

<400> SEQUENCE: 22

Leu Pro Val Leu Leu Ala Ala Pro
1 5

<210> SEQ ID NO 23
<211> LENGTH: 17
<212> TYPE: PRT
<213> ORGANISM: Artificial Sequence
<220> FEATURE:
<223> OTHER INFORMATION: membrane translocating peptide

<400> SEQUENCE: 23

Ala Ala Val Leu Leu Pro Val Leu Leu Ala Ala Lys Lys Lys Arg Lys
1 5 10 15

Ala

<210> SEQ ID NO 24
<211> LENGTH: 17
<212> TYPE: PRT
<213> ORGANISM: Artificial Sequence
<220> FEATURE:
<223> OTHER INFORMATION: membrane translocating peptide

<400> SEQUENCE: 24

Lys Lys Lys Arg Lys Ala Ala Ala Ala Val Leu Leu Pro Val Leu Leu
1 5 10 15

Ala

<210> SEQ ID NO 25
<211> LENGTH: 45
<212> TYPE: DNA
<213> ORGANISM: Artificial Sequence
<220> FEATURE:
<223> OTHER INFORMATION: encodes membrane translocating peptide
<220> FEATURE:
<221> NAME/KEY: misc_feature
<222> LOCATION: (3)..(3)
<223> OTHER INFORMATION: "r is A or G"
<220> FEATURE:
<221> NAME/KEY: misc_feature -continued
<222> LOCATION: (6)..(6)
<223> OTHER INFORMATION: "r is A or G"
<220> FEATURE:
<221> NAME/KEY: misc_feature
<222> LOCATION: (9)..(9)
<223> OTHER INFORMATION: "n is A or C or G or T"
<220> FEATURE:
<221> NAME/KEY: misc_feature
<222> LOCATION: (12)..(12)
<223> OTHER INFORMATION: "n is A or C or G or T"
<220> FEATURE:
<221> NAME/KEY: misc_feature
<222> LOCATION: (15)..(15)
<223> OTHER INFORMATION: "n is A or C or G or T"
<220> FEATURE:
<221> NAME/KEY: misc_feature
<222> LOCATION: (18)..(18)
<223> OTHER INFORMATION: "n is A or C or G or T"
<220> FEATURE:
<221> NAME/KEY: misc_feature
<222> LOCATION: (19)..(19)
<223> OTHER INFORMATION: "y is C or T"
<220> FEATURE:
<221> NAME/KEY: misc_feature
<222> LOCATION: (21)..(21)
<223> OTHER INFORMATION: "n is A or C or G or T"
<220> FEATURE:
<221> NAME/KEY: misc_feature
<222> LOCATION: (22)..(22)
<223> OTHER INFORMATION: "y is C or T"
<220> FEATURE:
<221> NAME/KEY: misc_feature
<222> LOCATION: (24)..(24)
<223> OTHER INFORMATION: "n is A or C or G or T"
<220> FEATURE:
<221> NAME/KEY: misc_feature
<222> LOCATION: (27)..(27)
<223> OTHER INFORMATION: "n is A or C or G or T"
<220> FEATURE:
<221> NAME/KEY: misc_feature
<222> LOCATION: (30)..(30)
<223> OTHER INFORMATION: "n is A or C or G or T"
<220> FEATURE:
<221> NAME/KEY: misc_feature
<222> LOCATION: (31)..(31)
<223> OTHER INFORMATION: "y is C or T"
<220> FEATURE:
<221> NAME/KEY: misc_feature
<222> LOCATION: (33)..(33)
<223> OTHER INFORMATION: "n is A or C or G or T"
<220> FEATURE:
<221> NAME/KEY: misc_feature
<222> LOCATION: (34)..(34)
<223> OTHER INFORMATION: "y is C or T"
<220> FEATURE:
<221> NAME/KEY: misc_feature
<222> LOCATION: (36)..(36)
<223> OTHER INFORMATION: "n is A or C or G or T"
<220> FEATURE:
<221> NAME/KEY: misc_feature
<222> LOCATION: (39)..(39)
<223> OTHER INFORMATION: "n is A or C or G or T"
<220> FEATURE:
<221> NAME/KEY: misc_feature
<222> LOCATION: (42)..(42)
<223> OTHER INFORMATION: "n is A or C or G or T"
<220> FEATURE:
<221> NAME/KEY: misc_feature
<222> LOCATION: (45)..(45)
<223> OTHER INFORMATION: "n is A or C or G or T"

<400> SEQUENCE: 25
aaraargcng cngcngtnyt nytnccngtn ytnytngcng cnccn 45

<210> SEQ ID NO 26
<211> LENGTH: 54
<212> TYPE: DNA

-continued

<213> ORGANISM: Artificial Sequence
<220> FEATURE:
<223> OTHER INFORMATION: encodes membrane translocating peptide
<220> FEATURE:
<221> NAME/KEY: misc_feature
<222> LOCATION: (1)..(1)
<223> OTHER INFORMATION: "y is C or T"
<220> FEATURE:
<221> NAME/KEY: misc_feature
<222> LOCATION: (3)..(3)
<223> OTHER INFORMATION: "n is A or C or G or T"
<220> FEATURE:
<221> NAME/KEY: misc_feature
<222> LOCATION: (6)..(6)
<223> OTHER INFORMATION: "y is C or T"
<220> FEATURE:
<221> NAME/KEY: misc_feature
<222> LOCATION: (9)..(9)
<223> OTHER INFORMATION: "r is A or G"
<220> FEATURE:
<221> NAME/KEY: misc_feature
<222> LOCATION: (12)..(12)
<223> OTHER INFORMATION: "r is A or G"
<220> FEATURE:
<221> NAME/KEY: misc_feature
<222> LOCATION: (15)..(15)
<223> OTHER INFORMATION: "r is A or G"
<220> FEATURE:
<221> NAME/KEY: misc_feature
<222> LOCATION: (18)..(18)
<223> OTHER INFORMATION: "n is A or C or G or T"
<220> FEATURE:
<221> NAME/KEY: misc_feature
<222> LOCATION: (21)..(21)
<223> OTHER INFORMATION: "n is A or C or G or T"
<220> FEATURE:
<221> NAME/KEY: misc_feature
<222> LOCATION: (24)..(24)
<223> OTHER INFORMATION: "n is A or C or G or T"
<220> FEATURE:
<221> NAME/KEY: misc_feature
<222> LOCATION: (27)..(27)
<223> OTHER INFORMATION: "n is A or C or G or T"
<220> FEATURE:
<221> NAME/KEY: misc_feature
<222> LOCATION: (28)..(28)
<223> OTHER INFORMATION: "y is C or T"
<220> FEATURE:
<221> NAME/KEY: misc_feature
<222> LOCATION: (30)..(30)
<223> OTHER INFORMATION: "n is A or C or G or T"
<220> FEATURE:
<221> NAME/KEY: misc_feature
<222> LOCATION: (31)..(31)
<223> OTHER INFORMATION: "y is C or T"
<220> FEATURE:
<221> NAME/KEY: misc_feature
<222> LOCATION: (33)..(33)
<223> OTHER INFORMATION: "n is A or C or G or T"
<220> FEATURE:
<221> NAME/KEY: misc_feature
<222> LOCATION: (36)..(36)
<223> OTHER INFORMATION: "n is A or C or G or T"
<220> FEATURE:
<221> NAME/KEY: misc_feature
<222> LOCATION: (39)..(39)
<223> OTHER INFORMATION: "n is A or C or G or T"
<220> FEATURE:
<221> NAME/KEY: misc_feature
<222> LOCATION: (40)..(40)
<223> OTHER INFORMATION: "y is C or T"
<220> FEATURE:
<221> NAME/KEY: misc_feature
<222> LOCATION: (42)..(42)
<223> OTHER INFORMATION: "n is A or C or G or T"
<220> FEATURE:
<221> NAME/KEY: misc_feature
<222> LOCATION: (43)..(43)
<223> OTHER INFORMATION: "y is C or T"

-continued

<220> FEATURE:
<221> NAME/KEY: misc_feature
<222> LOCATION: (45)..(45)
<223> OTHER INFORMATION: "n is A or C or G or T"
<220> FEATURE:
<221> NAME/KEY: misc_feature
<222> LOCATION: (48)..(48)
<223> OTHER INFORMATION: "n is A or C or G or T"
<220> FEATURE:
<221> NAME/KEY: misc_feature
<222> LOCATION: (51)..(51)
<223> OTHER INFORMATION: "n is A or C or G or T"
<220> FEATURE:
<221> NAME/KEY: misc_feature
<222> LOCATION: (54)..(54)
<223> OTHER INFORMATION: "n is A or C or G or T"

<400> SEQUENCE: 26
ytntgyaara araargcngc ngcngtnytn ytnccngtny tnytngcngc nccn 54

<210> SEQ ID NO 27
<211> LENGTH: 57
<212> TYPE: DNA
<213> ORGANISM: Artificial Sequence
<220> FEATURE:
<223> OTHER INFORMATION: encodes membrane translocating peptide
<220> FEATURE:
<221> NAME/KEY: misc_feature
<222> LOCATION: (3)..(3)
<223> OTHER INFORMATION: "r is A or G"
<220> FEATURE:
<221> NAME/KEY: misc_feature
<222> LOCATION: (6)..(6)
<223> OTHER INFORMATION: "r is A or G"
<220> FEATURE:
<221> NAME/KEY: misc_feature
<222> LOCATION: (9)..(9)
<223> OTHER INFORMATION: "n is A or C or G or T"
<220> FEATURE:
<221> NAME/KEY: misc_feature
<222> LOCATION: (12)..(12)
<223> OTHER INFORMATION: "n is A or C or G or T"
<220> FEATURE:
<221> NAME/KEY: misc_feature
<222> LOCATION: (15)..(15)
<223> OTHER INFORMATION: "n is A or C or G or T"
<220> FEATURE:
<221> NAME/KEY: misc_feature
<222> LOCATION: (18)..(18)
<223> OTHER INFORMATION: "n is A or C or G or T"
<220> FEATURE:
<221> NAME/KEY: misc_feature
<222> LOCATION: (19)..(19)
<223> OTHER INFORMATION: "y is C or T"
<220> FEATURE:
<221> NAME/KEY: misc_feature
<222> LOCATION: (21)..(21)
<223> OTHER INFORMATION: "n is A or C or G or T"
<220> FEATURE:
<221> NAME/KEY: misc_feature
<222> LOCATION: (22)..(22)
<223> OTHER INFORMATION: "y is C or T"
<220> FEATURE:
<221> NAME/KEY: misc_feature
<222> LOCATION: (24)..(24)
<223> OTHER INFORMATION: "n is A or C or G or T"
<220> FEATURE:
<221> NAME/KEY: misc_feature
<222> LOCATION: (27)..(27)
<223> OTHER INFORMATION: "n is A or C or G or T"
<220> FEATURE:
<221> NAME/KEY: misc_feature
<222> LOCATION: (30)..(30)
<223> OTHER INFORMATION: "n is A or C or G or T"
<220> FEATURE:
<221> NAME/KEY: misc_feature
<222> LOCATION: (31)..(31)

-continued

<223> OTHER INFORMATION: “y is C or T”
<220> FEATURE:
<221> NAME/KEY: misc_feature
<222> LOCATION: (33)..(33)
<223> OTHER INFORMATION: “n is A or C or G or T”
<220> FEATURE:
<221> NAME/KEY: misc_feature
<222> LOCATION: (34)..(34)
<223> OTHER INFORMATION: “y is C or T”
<220> FEATURE:
<221> NAME/KEY: misc_feature
<222> LOCATION: (36)..(36)
<223> OTHER INFORMATION: “n is A or C or G or T”
<220> FEATURE:
<221> NAME/KEY: misc_feature
<222> LOCATION: (39)..(39)
<223> OTHER INFORMATION: “n is A or C or G or T”
<220> FEATURE:
<221> NAME/KEY: misc_feature
<222> LOCATION: (42)..(42)
<223> OTHER INFORMATION: “n is A or C or G or T”
<220> FEATURE:
<221> NAME/KEY: misc_feature
<222> LOCATION: (45)..(45)
<223> OTHER INFORMATION: “n is A or C or G or T”
<220> FEATURE:
<221> NAME/KEY: misc_feature
<222> LOCATION: (46)..(46)
<223> OTHER INFORMATION: “m is A or C”
<220> FEATURE:
<221> NAME/KEY: misc_feature
<222> LOCATION: (48)..(48)
<223> OTHER INFORMATION: “n is A or C or G or T”
<220> FEATURE:
<221> NAME/KEY: misc_feature
<222> LOCATION: (51)..(51)
<223> OTHER INFORMATION: “r is A or G”
<220> FEATURE:
<221> NAME/KEY: misc_feature
<222> LOCATION: (54)..(54)
<223> OTHER INFORMATION: “y is C or T”
<220> FEATURE:
<221> NAME/KEY: misc_feature
<222> LOCATION: (55)..(55)
<223> OTHER INFORMATION: “y is C or T”
<220> FEATURE:
<221> NAME/KEY: misc_feature
<222> LOCATION: (57)..(57)
<223> OTHER INFORMATION: “n is A or C or G or T”

<400> SEQUENCE: 27
aaraargcng cngcngtnyt nytnccngtn ytnytngcng cnccnmgnga rgayytn 57

<210> SEQ ID NO 28
<211> LENGTH: 48
<212> TYPE: DNA
<213> ORGANISM: Artificial Sequence
<220> FEATURE:
<223> OTHER INFORMATION: encodes membrane translocating peptide
<220> FEATURE:
<221> NAME/KEY: misc_feature
<222> LOCATION: (3)..(3)
<223> OTHER INFORMATION: “r is A or G”
<220> FEATURE:
<221> NAME/KEY: misc_feature
<222> LOCATION: (6)..(6)
<223> OTHER INFORMATION: “r is A or G”
<220> FEATURE:
<221> NAME/KEY: misc_feature
<222> LOCATION: (9)..(9)
<223> OTHER INFORMATION: “y is C or T”
<220> FEATURE:
<221> NAME/KEY: misc_feature
<222> LOCATION: (12)..(12)
<223> OTHER INFORMATION: “n is A or C or G or T”
<220> FEATURE:
<221> NAME/KEY: misc_feature -continued
<222> LOCATION: (15)..(15)
<223> OTHER INFORMATION: “n is A or C or G or T”
<220> FEATURE:
<221> NAME/KEY: misc_feature
<222> LOCATION: (18)..(18)
<223> OTHER INFORMATION: “n is A or C or G or T”
<220> FEATURE:
<221> NAME/KEY: misc_feature
<222> LOCATION: (19)..(19)
<223> OTHER INFORMATION: “y is C or T”
<220> FEATURE:
<221> NAME/KEY: misc_feature
<222> LOCATION: (21)..(21)
<223> OTHER INFORMATION: “n is A or C or G or T”
<220> FEATURE:
<221> NAME/KEY: misc_feature
<222> LOCATION: (22)..(22)
<223> OTHER INFORMATION: “y is C or T”
<220> FEATURE:
<221> NAME/KEY: misc_feature
<222> LOCATION: (24)..(24)
<223> OTHER INFORMATION: “n is A or C or G or T”
<220> FEATURE:
<221> NAME/KEY: misc_feature
<222> LOCATION: (27)..(27)
<223> OTHER INFORMATION: “n is A or C or G or T”
<220> FEATURE:
<221> NAME/KEY: misc_feature
<222> LOCATION: (30)..(30)
<223> OTHER INFORMATION: “n is A or C or G or T”
<220> FEATURE:
<221> NAME/KEY: misc_feature
<222> LOCATION: (31)..(31)
<223> OTHER INFORMATION: “y is C or T”
<220> FEATURE:
<221> NAME/KEY: misc_feature
<222> LOCATION: (33)..(33)
<223> OTHER INFORMATION: “n is A or C or G or T”
<220> FEATURE:
<221> NAME/KEY: misc_feature
<222> LOCATION: (34)..(34)
<223> OTHER INFORMATION: “y is C or T”
<220> FEATURE:
<221> NAME/KEY: misc_feature
<222> LOCATION: (36)..(36)
<223> OTHER INFORMATION: “n is A or C or G or T”
<220> FEATURE:
<221> NAME/KEY: misc_feature
<222> LOCATION: (39)..(39)
<223> OTHER INFORMATION: “n is A or C or G or T”
<220> FEATURE:
<221> NAME/KEY: misc_feature
<222> LOCATION: (42)..(42)
<223> OTHER INFORMATION: “n is A or C or G or T”
<220> FEATURE:
<221> NAME/KEY: misc_feature
<222> LOCATION: (45)..(45)
<223> OTHER INFORMATION: “n is A or C or G or T”
<220> FEATURE:
<221> NAME/KEY: misc_feature
<222> LOCATION: (48)..(48)
<223> OTHER INFORMATION: “y is C or T”

<400> SEQUENCE: 28
aaraartgyg cngcngtnyt nytnccngtn ytnytngcng cnccntgy 48

<210> SEQ ID NO 29
<211> LENGTH: 39
<212> TYPE: DNA
<213> ORGANISM: Artificial Sequence
<220> FEATURE:
<223> OTHER INFORMATION: encodes membrane translocating peptide
<220> FEATURE:
<221> NAME/KEY: misc_feature
<222> LOCATION: (3)..(3)
<223> OTHER INFORMATION: “y is C or T”
<220> FEATURE:

-continued

<221> NAME/KEY: misc_feature
<222> LOCATION: (6)..(6)
<223> OTHER INFORMATION: "n is A or C or G or T"
<220> FEATURE:
<221> NAME/KEY: misc_feature
<222> LOCATION: (9)..(9)
<223> OTHER INFORMATION: "n is A or C or G or T"
<220> FEATURE:
<221> NAME/KEY: misc_feature
<222> LOCATION: (12)..(12)
<223> OTHER INFORMATION: "n is A or C or G or T"
<220> FEATURE:
<221> NAME/KEY: misc_feature
<222> LOCATION: (13)..(13)
<223> OTHER INFORMATION: "y is C or T"
<220> FEATURE:
<221> NAME/KEY: misc_feature
<222> LOCATION: (15)..(15)
<223> OTHER INFORMATION: "n is A or C or G or T"
<220> FEATURE:
<221> NAME/KEY: misc_feature
<222> LOCATION: (16)..(16)
<223> OTHER INFORMATION: "y is C or T"
<220> FEATURE:
<221> NAME/KEY: misc_feature
<222> LOCATION: (18)..(18)
<223> OTHER INFORMATION: "n is A or C or G or T"
<220> FEATURE:
<221> NAME/KEY: misc_feature
<222> LOCATION: (21)..(21)
<223> OTHER INFORMATION: "n is A or C or G or T"
<220> FEATURE:
<221> NAME/KEY: misc_feature
<222> LOCATION: (24)..(24)
<223> OTHER INFORMATION: "n is A or C or G or T"
<220> FEATURE:
<221> NAME/KEY: misc_feature
<222> LOCATION: (25)..(25)
<223> OTHER INFORMATION: "y is C or T"
<220> FEATURE:
<221> NAME/KEY: misc_feature
<222> LOCATION: (27)..(27)
<223> OTHER INFORMATION: "n is A or C or G or T"
<220> FEATURE:
<221> NAME/KEY: misc_feature
<222> LOCATION: (28)..(28)
<223> OTHER INFORMATION: "y is C or T"
<220> FEATURE:
<221> NAME/KEY: misc_feature
<222> LOCATION: (30)..(30)
<223> OTHER INFORMATION: "n is A or C or G or T"
<220> FEATURE:
<221> NAME/KEY: misc_feature
<222> LOCATION: (33)..(33)
<223> OTHER INFORMATION: "n is A or C or G or T"
<220> FEATURE:
<221> NAME/KEY: misc_feature
<222> LOCATION: (36)..(36)
<223> OTHER INFORMATION: "n is A or C or G or T"
<220> FEATURE:
<221> NAME/KEY: misc_feature
<222> LOCATION: (39)..(39)
<223> OTHER INFORMATION: "y is C or T"

<400> SEQUENCE: 29
tgygcngcng tnytnytncc ngtnytnytn gcngcntgy 39

<210> SEQ ID NO 30
<211> LENGTH: 36
<212> TYPE: DNA
<213> ORGANISM: Artificial Sequence
<220> FEATURE:
<223> OTHER INFORMATION: encodes membrane translocating peptide
<220> FEATURE:
<221> NAME/KEY: misc_feature
<222> LOCATION: (3)..(3)
<223> OTHER INFORMATION: "y is C or T"

-continued

<220> FEATURE:
<221> NAME/KEY: misc_feature
<222> LOCATION: (6)..(6)
<223> OTHER INFORMATION: “n is A or C or G or T”
<220> FEATURE:
<221> NAME/KEY: misc_feature
<222> LOCATION: (9)..(9)
<223> OTHER INFORMATION: “n is A or C or G or T”
<220> FEATURE:
<221> NAME/KEY: misc_feature
<222> LOCATION: (12)..(12)
<223> OTHER INFORMATION: “n is A or C or G or T”
<220> FEATURE:
<221> NAME/KEY: misc_feature
<222> LOCATION: (13)..(13)
<223> OTHER INFORMATION: “y is C or T”
<220> FEATURE:
<221> NAME/KEY: misc_feature
<222> LOCATION: (15)..(15)
<223> OTHER INFORMATION: “n is A or C or G or T”
<220> FEATURE:
<221> NAME/KEY: misc_feature
<222> LOCATION: (16)..(16)
<223> OTHER INFORMATION: “y is C or T”
<220> FEATURE:
<221> NAME/KEY: misc_feature
<222> LOCATION: (18)..(18)
<223> OTHER INFORMATION: “n is A or C or G or T”
<220> FEATURE:
<221> NAME/KEY: misc_feature
<222> LOCATION: (21)..(21)
<223> OTHER INFORMATION: “n is A or C or G or T”
<220> FEATURE:
<221> NAME/KEY: misc_feature
<222> LOCATION: (24)..(24)
<223> OTHER INFORMATION: “n is A or C or G or T”
<220> FEATURE:
<221> NAME/KEY: misc_feature
<222> LOCATION: (25)..(25)
<223> OTHER INFORMATION: “y is C or T”
<220> FEATURE:
<221> NAME/KEY: misc_feature
<222> LOCATION: (27)..(27)
<223> OTHER INFORMATION: “n is A or C or G or T”
<220> FEATURE:
<221> NAME/KEY: misc_feature
<222> LOCATION: (28)..(28)
<223> OTHER INFORMATION: “y is C or T”
<220> FEATURE:
<221> NAME/KEY: misc_feature
<222> LOCATION: (30)..(30)
<223> OTHER INFORMATION: “n is A or C or G or T”
<220> FEATURE:
<221> NAME/KEY: misc_feature
<222> LOCATION: (33)..(33)
<223> OTHER INFORMATION: “n is A or C or G or T”
<220> FEATURE:
<221> NAME/KEY: misc_feature
<222> LOCATION: (36)..(36)
<223> OTHER INFORMATION: “y is C or T”

<400> SEQUENCE: 30
tgygcngcng tnytnytncc ngtnytnytn gcntgy 36

<210> SEQ ID NO 31
<211> LENGTH: 33
<212> TYPE: DNA
<213> ORGANISM: Artificial Sequence
<220> FEATURE:
<223> OTHER INFORMATION: encodes membrane translocating peptide
<220> FEATURE:
<221> NAME/KEY: misc_feature
<222> LOCATION: (3)..(3)
<223> OTHER INFORMATION: “y is C or T”
<220> FEATURE:
<221> NAME/KEY: misc_feature
<222> LOCATION: (6)..(6)

-continued

<223> OTHER INFORMATION: "n is A or C or G or T"
<220> FEATURE:
<221> NAME/KEY: misc_feature
<222> LOCATION: (9)..(9)
<223> OTHER INFORMATION: "n is A or C or G or T"
<220> FEATURE:
<221> NAME/KEY: misc_feature
<222> LOCATION: (12)..(12)
<223> OTHER INFORMATION: "n is A or C or G or T"
<220> FEATURE:
<221> NAME/KEY: misc_feature
<222> LOCATION: (13)..(13)
<223> OTHER INFORMATION: "y is C or T"
<220> FEATURE:
<221> NAME/KEY: misc_feature
<222> LOCATION: (15)..(15)
<223> OTHER INFORMATION: "n is A or C or G or T"
<220> FEATURE:
<221> NAME/KEY: misc_feature
<222> LOCATION: (16)..(16)
<223> OTHER INFORMATION: "y is C or T"
<220> FEATURE:
<221> NAME/KEY: misc_feature
<222> LOCATION: (18)..(18)
<223> OTHER INFORMATION: "n is A or C or G or T"
<220> FEATURE:
<221> NAME/KEY: misc_feature
<222> LOCATION: (21)..(21)
<223> OTHER INFORMATION: "n is A or C or G or T"
<220> FEATURE:
<221> NAME/KEY: misc_feature
<222> LOCATION: (24)..(24)
<223> OTHER INFORMATION: "n is A or C or G or T"
<220> FEATURE:
<221> NAME/KEY: misc_feature
<222> LOCATION: (25)..(25)
<223> OTHER INFORMATION: "y is C or T"
<220> FEATURE:
<221> NAME/KEY: misc_feature
<222> LOCATION: (27)..(27)
<223> OTHER INFORMATION: "n is A or C or G or T"
<220> FEATURE:
<221> NAME/KEY: misc_feature
<222> LOCATION: (28)..(28)
<223> OTHER INFORMATION: "y is C or T"
<220> FEATURE:
<221> NAME/KEY: misc_feature
<222> LOCATION: (30)..(30)
<223> OTHER INFORMATION: "n is A or C or G or T"
<220> FEATURE:
<221> NAME/KEY: misc_feature
<222> LOCATION: (33)..(33)
<223> OTHER INFORMATION: "y is C or T"

<400> SEQUENCE: 31
tgygcngcng tnytnytncc ngtnytnytn tgy 33

<210> SEQ ID NO 32
<211> LENGTH: 30
<212> TYPE: DNA
<213> ORGANISM: Artificial Sequence
<220> FEATURE:
<223> OTHER INFORMATION: encodes membrane translocating peptide
<220> FEATURE:
<221> NAME/KEY: misc_feature
<222> LOCATION: (3)..(3)
<223> OTHER INFORMATION: "y is C or T"
<220> FEATURE:
<221> NAME/KEY: misc_feature
<222> LOCATION: (6)..(6)
<223> OTHER INFORMATION: "n is A or C or G or T"
<220> FEATURE:
<221> NAME/KEY: misc_feature
<222> LOCATION: (9)..(9)
<223> OTHER INFORMATION: "n is A or C or G or T"
<220> FEATURE:
<221> NAME/KEY: misc_feature
<222> LOCATION: (12)..(12)
<223> OTHER INFORMATION: "n is A or C or G or T"
<220> FEATURE:
<221> NAME/KEY: misc_feature
<222> LOCATION: (13)..(13)
<223> OTHER INFORMATION: "y is C or T"
<220> FEATURE:
<221> NAME/KEY: misc_feature
<222> LOCATION: (15)..(15)
<223> OTHER INFORMATION: "n is A or C or G or T"
<220> FEATURE:
<221> NAME/KEY: misc_feature
<222> LOCATION: (16)..(16)
<223> OTHER INFORMATION: "y is C or T"
<220> FEATURE:
<221> NAME/KEY: misc_feature
<222> LOCATION: (18)..(18)
<223> OTHER INFORMATION: "n is A or C or G or T"
<220> FEATURE:
<221> NAME/KEY: misc_feature
<222> LOCATION: (21)..(21)
<223> OTHER INFORMATION: "n is A or C or G or T"
<220> FEATURE:
<221> NAME/KEY: misc_feature
<222> LOCATION: (24)..(24)
<223> OTHER INFORMATION: "n is A or C or G or T"
<220> FEATURE:
<221> NAME/KEY: misc_feature
<222> LOCATION: (25)..(25)
<223> OTHER INFORMATION: "y is C or T"
<220> FEATURE:
<221> NAME/KEY: misc_feature
<222> LOCATION: (27)..(27)
<223> OTHER INFORMATION: "n is A or C or G or T"
<220> FEATURE:
<221> NAME/KEY: misc_feature
<222> LOCATION: (30)..(30)
<223> OTHER INFORMATION: "y is C or T"

<400> SEQUENCE: 32
tgygcngcng tnytnytncc ngtnytntgy 30

<210> SEQ ID NO 33
<211> LENGTH: 39
<212> TYPE: DNA
<213> ORGANISM: Artificial Sequence
<220> FEATURE:
<223> OTHER INFORMATION: encodes membrane translocating peptide
<220> FEATURE:
<221> NAME/KEY: misc_feature
<222> LOCATION: (3)..(3)
<223> OTHER INFORMATION: "y is C or T"
<220> FEATURE:
<221> NAME/KEY: misc_feature
<222> LOCATION: (6)..(6)
<223> OTHER INFORMATION: "n is A or C or G or T"
<220> FEATURE:
<221> NAME/KEY: misc_feature
<222> LOCATION: (9)..(9)
<223> OTHER INFORMATION: "n is A or C or G or T"
<220> FEATURE:
<221> NAME/KEY: misc_feature
<222> LOCATION: (10)..(10)
<223> OTHER INFORMATION: "y is C or T"
<220> FEATURE:
<221> NAME/KEY: misc_feature
<222> LOCATION: (12)..(12)
<223> OTHER INFORMATION: "n is A or C or G or T"
<220> FEATURE:
<221> NAME/KEY: misc_feature
<222> LOCATION: (13)..(13)
<223> OTHER INFORMATION: "y is C or T"
<220> FEATURE:
<221> NAME/KEY: misc_feature
<222> LOCATION: (15)..(15)
<223> OTHER INFORMATION: "n is A or C or G or T"
<220> FEATURE:

-continued

<221> NAME/KEY: misc_feature
<222> LOCATION: (18)..(18)
<223> OTHER INFORMATION: "n is A or C or G or T"
<220> FEATURE:
<221> NAME/KEY: misc_feature
<222> LOCATION: (21)..(21)
<223> OTHER INFORMATION: "n is A or C or G or T"
<220> FEATURE:
<221> NAME/KEY: misc_feature
<222> LOCATION: (22)..(22)
<223> OTHER INFORMATION: "y is C or T"
<220> FEATURE:
<221> NAME/KEY: misc_feature
<222> LOCATION: (24)..(24)
<223> OTHER INFORMATION: "n is A or C or G or T"
<220> FEATURE:
<221> NAME/KEY: misc_feature
<222> LOCATION: (25)..(25)
<223> OTHER INFORMATION: "y is C or T"
<220> FEATURE:
<221> NAME/KEY: misc_feature
<222> LOCATION: (27)..(27)
<223> OTHER INFORMATION: "n is A or C or G or T"
<220> FEATURE:
<221> NAME/KEY: misc_feature
<222> LOCATION: (30)..(30)
<223> OTHER INFORMATION: "n is A or C or G or T"
<220> FEATURE:
<221> NAME/KEY: misc_feature
<222> LOCATION: (33)..(33)
<223> OTHER INFORMATION: "n is A or C or G or T"
<220> FEATURE:
<221> NAME/KEY: misc_feature
<222> LOCATION: (36)..(36)
<223> OTHER INFORMATION: "n is A or C or G or T"
<220> FEATURE:
<221> NAME/KEY: misc_feature
<222> LOCATION: (39)..(39)
<223> OTHER INFORMATION: "y is C or T"

<400> SEQUENCE: 33
tgygcngtny tnytnccngt nytnytngcn gcnccntgy 39

<210> SEQ ID NO 34
<211> LENGTH: 36
<212> TYPE: DNA
<213> ORGANISM: Artificial Sequence
<220> FEATURE:
<223> OTHER INFORMATION: encodes membrane translocating peptide
<220> FEATURE:
<221> NAME/KEY: misc_feature
<222> LOCATION: (3)..(3)
<223> OTHER INFORMATION: "y is C or T"
<220> FEATURE:
<221> NAME/KEY: misc_feature
<222> LOCATION: (6)..(6)
<223> OTHER INFORMATION: "n is A or C or G or T"
<220> FEATURE:
<221> NAME/KEY: misc_feature
<222> LOCATION: (7)..(7)
<223> OTHER INFORMATION: "y is C or T"
<220> FEATURE:
<221> NAME/KEY: misc_feature
<222> LOCATION: (9)..(9)
<223> OTHER INFORMATION: "n is A or C or G or T"
<220> FEATURE:
<221> NAME/KEY: misc_feature
<222> LOCATION: (10)..(10)
<223> OTHER INFORMATION: "y is C or T"
<220> FEATURE:
<221> NAME/KEY: misc_feature
<222> LOCATION: (12)..(12)
<223> OTHER INFORMATION: "n is A or C or G or T"
<220> FEATURE:
<221> NAME/KEY: misc_feature
<222> LOCATION: (15)..(15)
<223> OTHER INFORMATION: "n is A or C or G or T"

-continued

<220> FEATURE:
<221> NAME/KEY: misc_feature
<222> LOCATION: (18)..(18)
<223> OTHER INFORMATION: "n is A or C or G or T"
<220> FEATURE:
<221> NAME/KEY: misc_feature
<222> LOCATION: (19)..(19)
<223> OTHER INFORMATION: "y is C or T"
<220> FEATURE:
<221> NAME/KEY: misc_feature
<222> LOCATION: (21)..(21)
<223> OTHER INFORMATION: "n is A or C or G or T"
<220> FEATURE:
<221> NAME/KEY: misc_feature
<222> LOCATION: (22)..(22)
<223> OTHER INFORMATION: "y is C or T"
<220> FEATURE:
<221> NAME/KEY: misc_feature
<222> LOCATION: (24)..(24)
<223> OTHER INFORMATION: "n is A or C or G or T"
<220> FEATURE:
<221> NAME/KEY: misc_feature
<222> LOCATION: (27)..(27)
<223> OTHER INFORMATION: "n is A or C or G or T"
<220> FEATURE:
<221> NAME/KEY: misc_feature
<222> LOCATION: (30)..(30)
<223> OTHER INFORMATION: "n is A or C or G or T"
<220> FEATURE:
<221> NAME/KEY: misc_feature
<222> LOCATION: (33)..(33)
<223> OTHER INFORMATION: "n is A or C or G or T"
<220> FEATURE:
<221> NAME/KEY: misc_feature
<222> LOCATION: (36)..(36)
<223> OTHER INFORMATION: "y is C or T"

<400> SEQUENCE: 34
tgygtnytny tnccngtnyt nytngcngcn ccntgy 36

<210> SEQ ID NO 35
<211> LENGTH: 33
<212> TYPE: DNA
<213> ORGANISM: Artificial Sequence
<220> FEATURE:
<223> OTHER INFORMATION: encodes membrane translocating peptide
<220> FEATURE:
<221> NAME/KEY: misc_feature
<222> LOCATION: (3)..(3)
<223> OTHER INFORMATION: "y is C or T"
<220> FEATURE:
<221> NAME/KEY: misc_feature
<222> LOCATION: (4)..(4)
<223> OTHER INFORMATION: "y is C or T"
<220> FEATURE:
<221> NAME/KEY: misc_feature
<222> LOCATION: (6)..(6)
<223> OTHER INFORMATION: "n is A or C or G or T"
<220> FEATURE:
<221> NAME/KEY: misc_feature
<222> LOCATION: (7)..(7)
<223> OTHER INFORMATION: "y is C or T"
<220> FEATURE:
<221> NAME/KEY: misc_feature
<222> LOCATION: (9)..(9)
<223> OTHER INFORMATION: "n is A or C or G or T"
<220> FEATURE:
<221> NAME/KEY: misc_feature
<222> LOCATION: (12)..(12)
<223> OTHER INFORMATION: "n is A or C or G or T"
<220> FEATURE:
<221> NAME/KEY: misc_feature
<222> LOCATION: (15)..(15)
<223> OTHER INFORMATION: "n is A or C or G or T"
<220> FEATURE:
<221> NAME/KEY: misc_feature
<222> LOCATION: (16)..(16)

-continued

<223> OTHER INFORMATION: “y is C or T”
<220> FEATURE:
<221> NAME/KEY: misc_feature
<222> LOCATION: (18)..(18)
<223> OTHER INFORMATION: “n is A or C or G or T”
<220> FEATURE:
<221> NAME/KEY: misc_feature
<222> LOCATION: (19)..(19)
<223> OTHER INFORMATION: “y is C or T”
<220> FEATURE:
<221> NAME/KEY: misc_feature
<222> LOCATION: (21)..(21)
<223> OTHER INFORMATION: “n is A or C or G or T”
<220> FEATURE:
<221> NAME/KEY: misc_feature
<222> LOCATION: (24)..(24)
<223> OTHER INFORMATION: “n is A or C or G or T”
<220> FEATURE:
<221> NAME/KEY: misc_feature
<222> LOCATION: (27)..(27)
<223> OTHER INFORMATION: “n is A or C or G or T”
<220> FEATURE:
<221> NAME/KEY: misc_feature
<222> LOCATION: (30)..(30)
<223> OTHER INFORMATION: “n is A or C or G or T”
<220> FEATURE:
<221> NAME/KEY: misc_feature
<222> LOCATION: (33)..(33)
<223> OTHER INFORMATION: “y is C or T”

<400> SEQUENCE: 35
tgyytnytnc cngtnytnyt ngcngcnccn tgy 33

<210> SEQ ID NO 36
<211> LENGTH: 30
<212> TYPE: DNA
<213> ORGANISM: Artificial Sequence
<220> FEATURE:
<223> OTHER INFORMATION: encodes membrane translocating peptide
<220> FEATURE:
<221> NAME/KEY: misc_feature
<222> LOCATION: (3)..(3)
<223> OTHER INFORMATION: “y is C or T”
<220> FEATURE:
<221> NAME/KEY: misc_feature
<222> LOCATION: (4)..(4)
<223> OTHER INFORMATION: “y is C or T”
<220> FEATURE:
<221> NAME/KEY: misc_feature
<222> LOCATION: (6)..(6)
<223> OTHER INFORMATION: “n is A or C or G or T”
<220> FEATURE:
<221> NAME/KEY: misc_feature
<222> LOCATION: (9)..(9)
<223> OTHER INFORMATION: “n is A or C or G or T”
<220> FEATURE:
<221> NAME/KEY: misc_feature
<222> LOCATION: (12)..(12)
<223> OTHER INFORMATION: “n is A or C or G or T”
<220> FEATURE:
<221> NAME/KEY: misc_feature
<222> LOCATION: (13)..(13)
<223> OTHER INFORMATION: “y is C or T”
<220> FEATURE:
<221> NAME/KEY: misc_feature
<222> LOCATION: (15)..(15)
<223> OTHER INFORMATION: “n is A or C or G or T”
<220> FEATURE:
<221> NAME/KEY: misc_feature
<222> LOCATION: (16)..(16)
<223> OTHER INFORMATION: “y is C or T”
<220> FEATURE:
<221> NAME/KEY: misc_feature
<222> LOCATION: (18)..(18)
<223> OTHER INFORMATION: “n is A or C or G or T”
<220> FEATURE:
<221> NAME/KEY: misc_feature -continued
<222> LOCATION: (21)..(21)
<223> OTHER INFORMATION: "n is A or C or G or T"
<220> FEATURE:
<221> NAME/KEY: misc_feature
<222> LOCATION: (24)..(24)
<223> OTHER INFORMATION: "n is A or C or G or T"
<220> FEATURE:
<221> NAME/KEY: misc_feature
<222> LOCATION: (27)..(27)
<223> OTHER INFORMATION: "n is A or C or G or T"
<220> FEATURE:
<221> NAME/KEY: misc_feature
<222> LOCATION: (30)..(30)
<223> OTHER INFORMATION: "y is C or T"

<400> SEQUENCE: 36
tgyytnccng tnytnytngc ngcnccntgy 30

<210> SEQ ID NO 37
<211> LENGTH: 36
<212> TYPE: DNA
<213> ORGANISM: Artificial Sequence
<220> FEATURE:
<223> OTHER INFORMATION: encodes membrane translocating peptide
<220> FEATURE:
<221> NAME/KEY: misc_feature
<222> LOCATION: (3)..(3)
<223> OTHER INFORMATION: "n is A or C or G or T"
<220> FEATURE:
<221> NAME/KEY: misc_feature
<222> LOCATION: (6)..(6)
<223> OTHER INFORMATION: "n is A or C or G or T"
<220> FEATURE:
<221> NAME/KEY: misc_feature
<222> LOCATION: (9)..(9)
<223> OTHER INFORMATION: "n is A or C or G or T"
<220> FEATURE:
<221> NAME/KEY: misc_feature
<222> LOCATION: (10)..(10)
<223> OTHER INFORMATION: "y is C or T"
<220> FEATURE:
<221> NAME/KEY: misc_feature
<222> LOCATION: (12)..(12)
<223> OTHER INFORMATION: "n is A or C or G or T"
<220> FEATURE:
<221> NAME/KEY: misc_feature
<222> LOCATION: (13)..(13)
<223> OTHER INFORMATION: "y is C or T"
<220> FEATURE:
<221> NAME/KEY: misc_feature
<222> LOCATION: (15)..(15)
<223> OTHER INFORMATION: "n is A or C or G or T"
<220> FEATURE:
<221> NAME/KEY: misc_feature
<222> LOCATION: (18)..(18)
<223> OTHER INFORMATION: "n is A or C or G or T"
<220> FEATURE:
<221> NAME/KEY: misc_feature
<222> LOCATION: (18)..(18)
<223> OTHER INFORMATION: "n is A or C or G or T"
<220> FEATURE:
<221> NAME/KEY: misc_feature
<222> LOCATION: (21)..(21)
<223> OTHER INFORMATION: "n is A or C or G or T"
<220> FEATURE:
<221> NAME/KEY: misc_feature
<222> LOCATION: (22)..(22)
<223> OTHER INFORMATION: "y is C or T"
<220> FEATURE:
<221> NAME/KEY: misc_feature
<222> LOCATION: (24)..(24)
<223> OTHER INFORMATION: "n is A or C or G or T"
<220> FEATURE:
<221> NAME/KEY: misc_feature
<222> LOCATION: (25)..(25)
<223> OTHER INFORMATION: "y is C or T"
<220> FEATURE:

-continued

<221> NAME/KEY: misc_feature
<222> LOCATION: (27)..(27)
<223> OTHER INFORMATION: "n is A or C or G or T"
<220> FEATURE:
<221> NAME/KEY: misc_feature
<222> LOCATION: (30)..(30)
<223> OTHER INFORMATION: "n is A or C or G or T"
<220> FEATURE:
<221> NAME/KEY: misc_feature
<222> LOCATION: (33)..(33)
<223> OTHER INFORMATION: "n is A or C or G or T"
<220> FEATURE:
<221> NAME/KEY: misc_feature
<222> LOCATION: (36)..(36)
<223> OTHER INFORMATION: "n is A or C or G or T"

<400> SEQUENCE: 37
gcngcngtny tnytnccngt nytnytngcn gcnccn 36

<210> SEQ ID NO 38
<211> LENGTH: 33
<212> TYPE: DNA
<213> ORGANISM: Artificial Sequence
<220> FEATURE:
<223> OTHER INFORMATION: encodes membrane translocating peptide
<220> FEATURE:
<221> NAME/KEY: misc_feature
<222> LOCATION: (3)..(3)
<223> OTHER INFORMATION: "n is A or C or G or T"
<220> FEATURE:
<221> NAME/KEY: misc_feature
<222> LOCATION: (6)..(6)
<223> OTHER INFORMATION: "n is A or C or G or T"
<220> FEATURE:
<221> NAME/KEY: misc_feature
<222> LOCATION: (9)..(9)
<223> OTHER INFORMATION: "n is A or C or G or T"
<220> FEATURE:
<221> NAME/KEY: misc_feature
<222> LOCATION: (10)..(10)
<223> OTHER INFORMATION: "y is C or T"
<220> FEATURE:
<221> NAME/KEY: misc_feature
<222> LOCATION: (12)..(12)
<223> OTHER INFORMATION: "n is A or C or G or T"
<220> FEATURE:
<221> NAME/KEY: misc_feature
<222> LOCATION: (13)..(13)
<223> OTHER INFORMATION: "y is C or T"
<220> FEATURE:
<221> NAME/KEY: misc_feature
<222> LOCATION: (15)..(15)
<223> OTHER INFORMATION: "n is A or C or G or T"
<220> FEATURE:
<221> NAME/KEY: misc_feature
<222> LOCATION: (18)..(18)
<223> OTHER INFORMATION: "n is A or C or G or T"
<220> FEATURE:
<221> NAME/KEY: misc_feature
<222> LOCATION: (21)..(21)
<223> OTHER INFORMATION: "n is A or C or G or T"
<220> FEATURE:
<221> NAME/KEY: misc_feature
<222> LOCATION: (22)..(22)
<223> OTHER INFORMATION: "y is C or T"
<220> FEATURE:
<221> NAME/KEY: misc_feature
<222> LOCATION: (24)..(24)
<223> OTHER INFORMATION: "n is A or C or G or T"
<220> FEATURE:
<221> NAME/KEY: misc_feature
<222> LOCATION: (25)..(25)
<223> OTHER INFORMATION: "y is C or T"
<220> FEATURE:
<221> NAME/KEY: misc_feature
<222> LOCATION: (27)..(27)
<223> OTHER INFORMATION: "n is A or C or G or T"

-continued

<220> FEATURE:
<221> NAME/KEY: misc_feature
<222> LOCATION: (30)..(30)
<223> OTHER INFORMATION: "n is A or C or G or T"
<220> FEATURE:
<221> NAME/KEY: misc_feature
<222> LOCATION: (33)..(33)
<223> OTHER INFORMATION: "n is A or C or G or T"

<400> SEQUENCE: 38
gcngcngtny tnytnccngt nytnytngcn gcn 33

<210> SEQ ID NO 39
<211> LENGTH: 36
<212> TYPE: DNA
<213> ORGANISM: Artificial Sequence
<220> FEATURE:
<223> OTHER INFORMATION: encodes membrane translocating peptide
<220> FEATURE:
<221> NAME/KEY: misc_feature
<222> LOCATION: (3)..(3)
<223> OTHER INFORMATION: "r is A or G"
<220> FEATURE:
<221> NAME/KEY: misc_feature
<222> LOCATION: (6)..(6)
<223> OTHER INFORMATION: "r is A or G"
<220> FEATURE:
<221> NAME/KEY: misc_feature
<222> LOCATION: (9)..(9)
<223> OTHER INFORMATION: "n is A or C or G or T"
<220> FEATURE:
<221> NAME/KEY: misc_feature
<222> LOCATION: (12)..(12)
<223> OTHER INFORMATION: "n is A or C or G or T"
<220> FEATURE:
<221> NAME/KEY: misc_feature
<222> LOCATION: (15)..(15)
<223> OTHER INFORMATION: "n is A or C or G or T"
<220> FEATURE:
<221> NAME/KEY: misc_feature
<222> LOCATION: (16)..(16)
<223> OTHER INFORMATION: "y is C or T"
<220> FEATURE:
<221> NAME/KEY: misc_feature
<222> LOCATION: (18)..(18)
<223> OTHER INFORMATION: "n is A or C or G or T"
<220> FEATURE:
<221> NAME/KEY: misc_feature
<222> LOCATION: (19)..(19)
<223> OTHER INFORMATION: "y is C or T"
<220> FEATURE:
<221> NAME/KEY: misc_feature
<222> LOCATION: (21)..(21)
<223> OTHER INFORMATION: "n is A or C or G or T"
<220> FEATURE:
<221> NAME/KEY: misc_feature
<222> LOCATION: (24)..(24)
<223> OTHER INFORMATION: "n is A or C or G or T"
<220> FEATURE:
<221> NAME/KEY: misc_feature
<222> LOCATION: (27)..(27)
<223> OTHER INFORMATION: "n is A or C or G or T"
<220> FEATURE:
<221> NAME/KEY: misc_feature
<222> LOCATION: (28)..(28)
<223> OTHER INFORMATION: "y is C or T"
<220> FEATURE:
<221> NAME/KEY: misc_feature
<222> LOCATION: (30)..(30)
<223> OTHER INFORMATION: "n is A or C or G or T"
<220> FEATURE:
<221> NAME/KEY: misc_feature
<222> LOCATION: (31)..(31)
<223> OTHER INFORMATION: "y is C or T"
<220> FEATURE:
<221> NAME/KEY: misc_feature
<222> LOCATION: (33)..(33)

-continued

```
<223> OTHER INFORMATION: "n is A or C or G or T"
<220> FEATURE:
<221> NAME/KEY: misc_feature
<222> LOCATION: (36)..(36)
<223> OTHER INFORMATION: "n is A or C or G or T"

<400> SEQUENCE: 39

aaraargcng cngtnytnyt nccngtnytn ytngcn                    36


<210> SEQ ID NO 40
<211> LENGTH: 27
<212> TYPE: DNA
<213> ORGANISM: Artificial Sequence
<220> FEATURE:
<223> OTHER INFORMATION: encodes membrane translocating peptide
<220> FEATURE:
<221> NAME/KEY: misc_feature
<222> LOCATION: (3)..(3)
<223> OTHER INFORMATION: "n is A or C or G or T"
<220> FEATURE:
<221> NAME/KEY: misc_feature
<222> LOCATION: (6)..(6)
<223> OTHER INFORMATION: "n is A or C or G or T"
<220> FEATURE:
<221> NAME/KEY: misc_feature
<222> LOCATION: (9)..(9)
<223> OTHER INFORMATION: "n is A or C or G or T"
<220> FEATURE:
<221> NAME/KEY: misc_feature
<222> LOCATION: (10)..(10)
<223> OTHER INFORMATION: "y is C or T"
<220> FEATURE:
<221> NAME/KEY: misc_feature
<222> LOCATION: (12)..(12)
<223> OTHER INFORMATION: "n is A or C or G or T"
<220> FEATURE:
<221> NAME/KEY: misc_feature
<222> LOCATION: (13)..(13)
<223> OTHER INFORMATION: "y is C or T"
<220> FEATURE:
<221> NAME/KEY: misc_feature
<222> LOCATION: (15)..(15)
<223> OTHER INFORMATION: "n is A or C or G or T"
<220> FEATURE:
<221> NAME/KEY: misc_feature
<222> LOCATION: (18)..(18)
<223> OTHER INFORMATION: "n is A or C or G or T"
<220> FEATURE:
<221> NAME/KEY: misc_feature
<222> LOCATION: (21)..(21)
<223> OTHER INFORMATION: "n is A or C or G or T"
<220> FEATURE:
<221> NAME/KEY: misc_feature
<222> LOCATION: (22)..(22)
<223> OTHER INFORMATION: "y is C or T"
<220> FEATURE:
<221> NAME/KEY: misc_feature
<222> LOCATION: (24)..(24)
<223> OTHER INFORMATION: "n is A or C or G or T"
<220> FEATURE:
<221> NAME/KEY: misc_feature
<222> LOCATION: (25)..(25)
<223> OTHER INFORMATION: "y is C or T"
<220> FEATURE:
<221> NAME/KEY: misc_feature
<222> LOCATION: (27)..(27)
<223> OTHER INFORMATION: "n is A or C or G or T"

<400> SEQUENCE: 40

gcngcngtny tnytnccngt nytnytn                              27


<210> SEQ ID NO 41
<211> LENGTH: 27
<212> TYPE: DNA
<213> ORGANISM: Artificial Sequence
```

-continued

<220> FEATURE:
<223> OTHER INFORMATION: encodes membrane translocating peptide
<220> FEATURE:
<221> NAME/KEY: misc_feature
<222> LOCATION: (3)..(3)
<223> OTHER INFORMATION: "n is A or C or G or T"
<220> FEATURE:
<221> NAME/KEY: misc_feature
<222> LOCATION: (6)..(6)
<223> OTHER INFORMATION: "n is A or C or G or T"
<220> FEATURE:
<221> NAME/KEY: misc_feature
<222> LOCATION: (9)..(9)
<223> OTHER INFORMATION: "n is A or C or G or T"
<220> FEATURE:
<221> NAME/KEY: misc_feature
<222> LOCATION: (10)..(10)
<223> OTHER INFORMATION: "y is C or T"
<220> FEATURE:
<221> NAME/KEY: misc_feature
<222> LOCATION: (12)..(12)
<223> OTHER INFORMATION: "n is A or C or G or T"
<220> FEATURE:
<221> NAME/KEY: misc_feature
<222> LOCATION: (13)..(13)
<223> OTHER INFORMATION: "y is C or T"
<220> FEATURE:
<221> NAME/KEY: misc_feature
<222> LOCATION: (15)..(15)
<223> OTHER INFORMATION: "n is A or C or G or T"
<220> FEATURE:
<221> NAME/KEY: misc_feature
<222> LOCATION: (18)..(18)
<223> OTHER INFORMATION: "n is A or C or G or T"
<220> FEATURE:
<221> NAME/KEY: misc_feature
<222> LOCATION: (21)..(21)
<223> OTHER INFORMATION: "n is A or C or G or T"
<220> FEATURE:
<221> NAME/KEY: misc_feature
<222> LOCATION: (22)..(22)
<223> OTHER INFORMATION: "y is C or T"
<220> FEATURE:
<221> NAME/KEY: misc_feature
<222> LOCATION: (24)..(24)
<223> OTHER INFORMATION: "n is A or C or G or T"
<220> FEATURE:
<221> NAME/KEY: misc_feature
<222> LOCATION: (25)..(25)
<223> OTHER INFORMATION: "y is C or T"
<220> FEATURE:
<221> NAME/KEY: misc_feature
<222> LOCATION: (27)..(27)
<223> OTHER INFORMATION: "n is A or C or G or T"

<400> SEQUENCE: 41
gcngcngtny tnytnccngt nytnytn 27

<210> SEQ ID NO 42
<211> LENGTH: 33
<212> TYPE: DNA
<213> ORGANISM: Artificial Sequence
<220> FEATURE:
<223> OTHER INFORMATION: encodes membrane translocating peptide
<220> FEATURE:
<221> NAME/KEY: misc_feature
<222> LOCATION: (3)..(3)
<223> OTHER INFORMATION: "n is A or C or G or T"
<220> FEATURE:
<221> NAME/KEY: misc_feature
<222> LOCATION: (6)..(6)
<223> OTHER INFORMATION: "n is A or C or G or T"
<220> FEATURE:
<221> NAME/KEY: misc_feature
<222> LOCATION: (7)..(7)
<223> OTHER INFORMATION: "y is C or T"
<220> FEATURE:

-continued

<221> NAME/KEY: misc_feature
<222> LOCATION: (9)..(9)
<223> OTHER INFORMATION: "n is A or C or G or T"
<220> FEATURE:
<221> NAME/KEY: misc_feature
<222> LOCATION: (10)..(10)
<223> OTHER INFORMATION: "y is C or T"
<220> FEATURE:
<221> NAME/KEY: misc_feature
<222> LOCATION: (12)..(12)
<223> OTHER INFORMATION: "n is A or C or G or T"
<220> FEATURE:
<221> NAME/KEY: misc_feature
<222> LOCATION: (15)..(15)
<223> OTHER INFORMATION: "n is A or C or G or T"
<220> FEATURE:
<221> NAME/KEY: misc_feature
<222> LOCATION: (18)..(18)
<223> OTHER INFORMATION: "n is A or C or G or T"
<220> FEATURE:
<221> NAME/KEY: misc_feature
<222> LOCATION: (19)..(19)
<223> OTHER INFORMATION: "y is C or T"
<220> FEATURE:
<221> NAME/KEY: misc_feature
<222> LOCATION: (21)..(21)
<223> OTHER INFORMATION: "n is A or C or G or T"
<220> FEATURE:
<221> NAME/KEY: misc_feature
<222> LOCATION: (22)..(22)
<223> OTHER INFORMATION: "y is C or T"
<220> FEATURE:
<221> NAME/KEY: misc_feature
<222> LOCATION: (24)..(24)
<223> OTHER INFORMATION: "n is A or C or G or T"
<220> FEATURE:
<221> NAME/KEY: misc_feature
<222> LOCATION: (27)..(27)
<223> OTHER INFORMATION: "n is A or C or G or T"
<220> FEATURE:
<221> NAME/KEY: misc_feature
<222> LOCATION: (30)..(30)
<223> OTHER INFORMATION: "n is A or C or G or T"
<220> FEATURE:
<221> NAME/KEY: misc_feature
<222> LOCATION: (33)..(33)
<223> OTHER INFORMATION: "n is A or C or G or T"

<400> SEQUENCE: 42
gcngtnytny tnccngtnyt nytngcngcn ccn 33

<210> SEQ ID NO 43
<211> LENGTH: 30
<212> TYPE: DNA
<213> ORGANISM: Artificial Sequence
<220> FEATURE:
<223> OTHER INFORMATION: encodes membrane translocating peptide
<220> FEATURE:
<221> NAME/KEY: misc_feature
<222> LOCATION: (3)..(3)
<223> OTHER INFORMATION: "n is A or C or G or T"
<220> FEATURE:
<221> NAME/KEY: misc_feature
<222> LOCATION: (4)..(4)
<223> OTHER INFORMATION: "y is C or T"
<220> FEATURE:
<221> NAME/KEY: misc_feature
<222> LOCATION: (6)..(6)
<223> OTHER INFORMATION: "n is A or C or G or T"
<220> FEATURE:
<221> NAME/KEY: misc_feature
<222> LOCATION: (7)..(7)
<223> OTHER INFORMATION: "y is C or T"
<220> FEATURE:
<221> NAME/KEY: misc_feature
<222> LOCATION: (9)..(9)
<223> OTHER INFORMATION: "n is A or C or G or T"

-continued

<220> FEATURE:
<221> NAME/KEY: misc_feature
<222> LOCATION: (12)..(12)
<223> OTHER INFORMATION: "n is A or C or G or T"
<220> FEATURE:
<221> NAME/KEY: misc_feature
<222> LOCATION: (15)..(15)
<223> OTHER INFORMATION: "n is A or C or G or T"
<220> FEATURE:
<221> NAME/KEY: misc_feature
<222> LOCATION: (16)..(16)
<223> OTHER INFORMATION: "y is C or T"
<220> FEATURE:
<221> NAME/KEY: misc_feature
<222> LOCATION: (18)..(18)
<223> OTHER INFORMATION: "n is A or C or G or T"
<220> FEATURE:
<221> NAME/KEY: misc_feature
<222> LOCATION: (19)..(19)
<223> OTHER INFORMATION: "y is C or T"
<220> FEATURE:
<221> NAME/KEY: misc_feature
<222> LOCATION: (21)..(21)
<223> OTHER INFORMATION: "n is A or C or G or T"
<220> FEATURE:
<221> NAME/KEY: misc_feature
<222> LOCATION: (24)..(24)
<223> OTHER INFORMATION: "n is A or C or G or T"
<220> FEATURE:
<221> NAME/KEY: misc_feature
<222> LOCATION: (27)..(27)
<223> OTHER INFORMATION: "n is A or C or G or T"
<220> FEATURE:
<221> NAME/KEY: misc_feature
<222> LOCATION: (30)..(30)
<223> OTHER INFORMATION: "n is A or C or G or T"

<400> SEQUENCE: 43
gtnytnytnc cngtnytnyt ngcngcnccn 30

<210> SEQ ID NO 44
<211> LENGTH: 27
<212> TYPE: DNA
<213> ORGANISM: Artificial Sequence
<220> FEATURE:
<223> OTHER INFORMATION: encodes membrane translocating peptide
<220> FEATURE:
<221> NAME/KEY: misc_feature
<222> LOCATION: (1)..(1)
<223> OTHER INFORMATION: "y is C or T"
<220> FEATURE:
<221> NAME/KEY: misc_feature
<222> LOCATION: (3)..(3)
<223> OTHER INFORMATION: "n is for A or C or G or T"
<220> FEATURE:
<221> NAME/KEY: misc_feature
<222> LOCATION: (4)..(4)
<223> OTHER INFORMATION: "y is C or T"
<220> FEATURE:
<221> NAME/KEY: misc_feature
<222> LOCATION: (6)..(6)
<223> OTHER INFORMATION: "n is for A or C or G or T"
<220> FEATURE:
<221> NAME/KEY: misc_feature
<222> LOCATION: (9)..(9)
<223> OTHER INFORMATION: "n is for A or C or G or T"
<220> FEATURE:
<221> NAME/KEY: misc_feature
<222> LOCATION: (12)..(12)
<223> OTHER INFORMATION: "n is for A or C or G or T"
<220> FEATURE:
<221> NAME/KEY: misc_feature
<222> LOCATION: (13)..(13)
<223> OTHER INFORMATION: "y is C or T"
<220> FEATURE:
<221> NAME/KEY: misc_feature
<222> LOCATION: (15)..(15)

-continued

<223> OTHER INFORMATION: "n is for A or C or G or T"
<220> FEATURE:
<221> NAME/KEY: misc_feature
<222> LOCATION: (16)..(16)
<223> OTHER INFORMATION: "y is C or T"
<220> FEATURE:
<221> NAME/KEY: misc_feature
<222> LOCATION: (18)..(18)
<223> OTHER INFORMATION: "n is for A or C or G or T"
<220> FEATURE:
<221> NAME/KEY: misc_feature
<222> LOCATION: (21)..(21)
<223> OTHER INFORMATION: "n is for A or C or G or T"
<220> FEATURE:
<221> NAME/KEY: misc_feature
<222> LOCATION: (24)..(24)
<223> OTHER INFORMATION: "n is for A or C or G or T"
<220> FEATURE:
<221> NAME/KEY: misc_feature
<222> LOCATION: (27)..(27)
<223> OTHER INFORMATION: "n is for A or C or G or T"

<400> SEQUENCE: 44
ytnytnccng tnytnytngc ngcnccn 27

<210> SEQ ID NO 45
<211> LENGTH: 24
<212> TYPE: DNA
<213> ORGANISM: Artificial Sequence
<220> FEATURE:
<223> OTHER INFORMATION: encodes membrane translocating peptide
<220> FEATURE:
<221> NAME/KEY: misc_feature
<222> LOCATION: (1)..(1)
<223> OTHER INFORMATION: "y is C or T"
<220> FEATURE:
<221> NAME/KEY: misc_feature
<222> LOCATION: (3)..(3)
<223> OTHER INFORMATION: "n is A or C or G or T"
<220> FEATURE:
<221> NAME/KEY: misc_feature
<222> LOCATION: (6)..(6)
<223> OTHER INFORMATION: "n is A or C or G or T"
<220> FEATURE:
<221> NAME/KEY: misc_feature
<222> LOCATION: (9)..(9)
<223> OTHER INFORMATION: "n is A or C or G or T"
<220> FEATURE:
<221> NAME/KEY: misc_feature
<222> LOCATION: (10)..(10)
<223> OTHER INFORMATION: "y is C or T"
<220> FEATURE:
<221> NAME/KEY: misc_feature
<222> LOCATION: (12)..(12)
<223> OTHER INFORMATION: "n is A or C or G or T"
<220> FEATURE:
<221> NAME/KEY: misc_feature
<222> LOCATION: (13)..(13)
<223> OTHER INFORMATION: "y is C or T"
<220> FEATURE:
<221> NAME/KEY: misc_feature
<222> LOCATION: (15)..(15)
<223> OTHER INFORMATION: "n is A or C or G or T"
<220> FEATURE:
<221> NAME/KEY: misc_feature
<222> LOCATION: (18)..(18)
<223> OTHER INFORMATION: "n is A or C or G or T"
<220> FEATURE:
<221> NAME/KEY: misc_feature
<222> LOCATION: (21)..(21)
<223> OTHER INFORMATION: "n is A or C or G or T"
<220> FEATURE:
<221> NAME/KEY: misc_feature
<222> LOCATION: (24)..(24)
<223> OTHER INFORMATION: "n is A or C or G or T"

<400> SEQUENCE: 45

-continued ytnccngtny tnytngcngc nccn 24

<210> SEQ ID NO 46
<211> LENGTH: 50
<212> TYPE: DNA
<213> ORGANISM: Artificial Sequence
<220> FEATURE:
<223> OTHER INFORMATION: encodes membrane translocating peptide
<220> FEATURE:
<221> NAME/KEY: misc_feature
<222> LOCATION: (2)..(2)
<223> OTHER INFORMATION: "n is A or C or G or T"
<220> FEATURE:
<221> NAME/KEY: misc_feature
<222> LOCATION: (5)..(5)
<223> OTHER INFORMATION: "n is A or C or G or T"
<220> FEATURE:
<221> NAME/KEY: misc_feature
<222> LOCATION: (8)..(8)
<223> OTHER INFORMATION: "n is A or C or G or T"
<220> FEATURE:
<221> NAME/KEY: misc_feature
<222> LOCATION: (9)..(9)
<223> OTHER INFORMATION: "y is C or T"
<220> FEATURE:
<221> NAME/KEY: misc_feature
<222> LOCATION: (11)..(11)
<223> OTHER INFORMATION: "n is A or C or G or T"
<220> FEATURE:
<221> NAME/KEY: misc_feature
<222> LOCATION: (12)..(12)
<223> OTHER INFORMATION: "y is C or T"
<220> FEATURE:
<221> NAME/KEY: misc_feature
<222> LOCATION: (14)..(14)
<223> OTHER INFORMATION: "n is A or C or G or T"
<220> FEATURE:
<221> NAME/KEY: misc_feature
<222> LOCATION: (17)..(17)
<223> OTHER INFORMATION: "n is A or C or G or T"
<220> FEATURE:
<221> NAME/KEY: misc_feature
<222> LOCATION: (20)..(20)
<223> OTHER INFORMATION: "n is A or C or G or T"
<220> FEATURE:
<221> NAME/KEY: misc_feature
<222> LOCATION: (21)..(21)
<223> OTHER INFORMATION: "y is C or T"
<220> FEATURE:
<221> NAME/KEY: misc_feature
<222> LOCATION: (23)..(23)
<223> OTHER INFORMATION: "n is A or C or G or T"
<220> FEATURE:
<221> NAME/KEY: misc_feature
<222> LOCATION: (24)..(24)
<223> OTHER INFORMATION: "y is C or T"
<220> FEATURE:
<221> NAME/KEY: misc_feature
<222> LOCATION: (26)..(26)
<223> OTHER INFORMATION: "n is A or C or G or T"
<220> FEATURE:
<221> NAME/KEY: misc_feature
<222> LOCATION: (29)..(29)
<223> OTHER INFORMATION: "n is A or C or G or T"
<220> FEATURE:
<221> NAME/KEY: misc_feature
<222> LOCATION: (32)..(32)
<223> OTHER INFORMATION: "n is A or C or G or T"
<220> FEATURE:
<221> NAME/KEY: misc_feature
<222> LOCATION: (35)..(35)
<223> OTHER INFORMATION: "r is A or G"
<220> FEATURE:
<221> NAME/KEY: misc_feature
<222> LOCATION: (38)..(38)
<223> OTHER INFORMATION: "r is A or G"
<220> FEATURE:

-continued

<221> NAME/KEY: misc_feature
<222> LOCATION: (41)..(41)
<223> OTHER INFORMATION: "r is A or G"
<220> FEATURE:
<221> NAME/KEY: misc_feature
<222> LOCATION: (42)..(42)
<223> OTHER INFORMATION: "m is A or C"
<220> FEATURE:
<221> NAME/KEY: misc_feature
<222> LOCATION: (44)..(44)
<223> OTHER INFORMATION: "n is A or C or G or T"
<220> FEATURE:
<221> NAME/KEY: misc_feature
<222> LOCATION: (47)..(47)
<223> OTHER INFORMATION: "r is A or G"
<220> FEATURE:
<221> NAME/KEY: misc_feature
<222> LOCATION: (50)..(50)
<223> OTHER INFORMATION: "n is A or C or G or T"

<400> SEQUENCE: 46
cngcngtnyt nytnccngtn ytnytngcng cnaaraaraa rmgnaargcn 50

<210> SEQ ID NO 47
<211> LENGTH: 51
<212> TYPE: DNA
<213> ORGANISM: Artificial Sequence
<220> FEATURE:
<223> OTHER INFORMATION: encodes membrane translocating peptide
<220> FEATURE:
<221> NAME/KEY: misc_feature
<222> LOCATION: (3)..(3)
<223> OTHER INFORMATION: "r is A or G"
<220> FEATURE:
<221> NAME/KEY: misc_feature
<222> LOCATION: (6)..(6)
<223> OTHER INFORMATION: "r is A or G"
<220> FEATURE:
<221> NAME/KEY: misc_feature
<222> LOCATION: (9)..(9)
<223> OTHER INFORMATION: "r is A or G"
<220> FEATURE:
<221> NAME/KEY: misc_feature
<222> LOCATION: (10)..(10)
<223> OTHER INFORMATION: "m is A or C"
<220> FEATURE:
<221> NAME/KEY: misc_feature
<222> LOCATION: (12)..(12)
<223> OTHER INFORMATION: "n is A or C or G or T"
<220> FEATURE:
<221> NAME/KEY: misc_feature
<222> LOCATION: (15)..(15)
<223> OTHER INFORMATION: "r is A or G"
<220> FEATURE:
<221> NAME/KEY: misc_feature
<222> LOCATION: (18)..(18)
<223> OTHER INFORMATION: "n is A or C or G or T"
<220> FEATURE:
<221> NAME/KEY: misc_feature
<222> LOCATION: (21)..(21)
<223> OTHER INFORMATION: "n is A or C or G or T"
<220> FEATURE:
<221> NAME/KEY: misc_feature
<222> LOCATION: (24)..(24)
<223> OTHER INFORMATION: "n is A or C or G or T"
<220> FEATURE:
<221> NAME/KEY: misc_feature
<222> LOCATION: (27)..(27)
<223> OTHER INFORMATION: "n is A or C or G or T"
<220> FEATURE:
<221> NAME/KEY: misc_feature
<222> LOCATION: (30)..(30)
<223> OTHER INFORMATION: "n is A or C or G or T"
<220> FEATURE:
<221> NAME/KEY: misc_feature
<222> LOCATION: (31)..(31)
<223> OTHER INFORMATION: "y is C or T"

-continued

<220> FEATURE:
<221> NAME/KEY: misc_feature
<222> LOCATION: (33)..(33)
<223> OTHER INFORMATION: "n is A or C or G or T"
<220> FEATURE:
<221> NAME/KEY: misc_feature
<222> LOCATION: (34)..(34)
<223> OTHER INFORMATION: "y is C or T"
<220> FEATURE:
<221> NAME/KEY: misc_feature
<222> LOCATION: (36)..(36)
<223> OTHER INFORMATION: "n is A or C or G or T"
<220> FEATURE:
<221> NAME/KEY: misc_feature
<222> LOCATION: (39)..(39)
<223> OTHER INFORMATION: "n is A or C or G or T"
<220> FEATURE:
<221> NAME/KEY: misc_feature
<222> LOCATION: (42)..(42)
<223> OTHER INFORMATION: "n is A or C or G or T"
<220> FEATURE:
<221> NAME/KEY: misc_feature
<222> LOCATION: (43)..(43)
<223> OTHER INFORMATION: "y is C or T"
<220> FEATURE:
<221> NAME/KEY: misc_feature
<222> LOCATION: (45)..(45)
<223> OTHER INFORMATION: "n is A or C or G or T"
<220> FEATURE:
<221> NAME/KEY: misc_feature
<222> LOCATION: (46)..(46)
<223> OTHER INFORMATION: "y is C or T"
<220> FEATURE:
<221> NAME/KEY: misc_feature
<222> LOCATION: (48)..(48)
<223> OTHER INFORMATION: "n is A or C or G or T"
<220> FEATURE:
<221> NAME/KEY: misc_feature
<222> LOCATION: (51)..(51)
<223> OTHER INFORMATION: "n is A or C or G or T"

<400> SEQUENCE: 47
aaraaraarm gnaargcngc ngcngcngtn ytnytnccng tnytnytngc n 51

<210> SEQ ID NO 48
<211> LENGTH: 16
<212> TYPE: PRT
<213> ORGANISM: Artificial Sequence
<220> FEATURE:
<223> OTHER INFORMATION: dansylated membrane translocating peptide
<220> FEATURE:
<221> NAME/KEY: MOD_RES
<222> LOCATION: (1)..(1)
<223> OTHER INFORMATION: dansylated

<400> SEQUENCE: 48

Lys Lys Lys Ala Ala Ala Val Leu Leu Pro Val Leu Leu Ala Ala Pro
1 5 10 15

<210> SEQ ID NO 49
<211> LENGTH: 44
<212> TYPE: PRT
<213> ORGANISM: Artificial Sequence
<220> FEATURE:
<223> OTHER INFORMATION: dansylated membrane translocating peptide
<220> FEATURE:
<221> NAME/KEY: MOD_RES
<222> LOCATION: (1)..(1)
<223> OTHER INFORMATION: dansylated

<400> SEQUENCE: 49

Lys Ser Asp His Ala Leu Gly Thr Asn Leu Arg Ser Asp Asn Ala Lys
1 5 10 15

-continued

```
Glu Pro Gly Asp Tyr Asn Cys Cys Gly Asn Gly Asn Ser Thr Gly Arg
            20                  25                  30

Lys Val Phe Asn Arg Arg Arg Ser Ala Ile Pro Tyr
        35                  40


<210> SEQ ID NO 50
<211> LENGTH: 15
<212> TYPE: PRT
<213> ORGANISM: Artificial Sequence
<220> FEATURE:
<223> OTHER INFORMATION: dansylated membrane translocating peptide
<220> FEATURE:
<221> NAME/KEY: MOD_RES
<222> LOCATION: (1)..(1)
<223> OTHER INFORMATION: dansylated

<400> SEQUENCE: 50

Lys Pro Gly Asp Tyr Asn Cys Cys Gly Asn Gly Asn Ser Thr Gly
1               5                   10                  15


<210> SEQ ID NO 51
<211> LENGTH: 41
<212> TYPE: PRT
<213> ORGANISM: Artificial Sequence
<220> FEATURE:
<223> OTHER INFORMATION: dansylated membrane translocating peptide
<220> FEATURE:
<221> NAME/KEY: MOD_RES
<222> LOCATION: (1)..(1)
<223> OTHER INFORMATION: dansylated

<400> SEQUENCE: 51

Lys Leu Ser Thr Pro Pro Ser Arg Glu Ala Tyr Ser Arg Pro Tyr Ser
1               5                   10                  15

Val Asp Ser Asp Ser Asp Thr Asn Ala Lys His Ser Ser His Asn Arg
            20                  25                  30

Arg Leu Arg Thr Arg Ser Arg Pro Asn
        35                  40


<210> SEQ ID NO 52
<211> LENGTH: 18
<212> TYPE: PRT
<213> ORGANISM: Artificial Sequence
<220> FEATURE:
<223> OTHER INFORMATION: dansylated cyclic D form peptide
<220> FEATURE:
<221> NAME/KEY: MOD_RES
<222> LOCATION: (1)..(1)
<223> OTHER INFORMATION: dansylated
<220> FEATURE:
<221> NAME/KEY: MISC_FEATURE
<222> LOCATION: (3)..(3)
<223> OTHER INFORMATION: D form amino acid
<220> FEATURE:
<221> NAME/KEY: MISC_FEATURE
<222> LOCATION: (7)..(7)
<223> OTHER INFORMATION: D form amino acid
<220> FEATURE:
<221> NAME/KEY: MISC_FEATURE
<222> LOCATION: (11)..(11)
<223> OTHER INFORMATION: D form amino acid
<220> FEATURE:
<221> NAME/KEY: MISC_FEATURE
<222> LOCATION: (13)..(13)
<223> OTHER INFORMATION: D form amino acid
<220> FEATURE:
<221> NAME/KEY: MISC_FEATURE
<222> LOCATION: (14)..(14)
<223> OTHER INFORMATION: D form amino acid

<400> SEQUENCE: 52
```

-continued

```
Lys Lys Thr Arg Lys Ser Ser Arg Ser Asn Pro Arg Gly Arg Arg His
1               5                   10                  15

Pro Gly


<210> SEQ ID NO 53
<211> LENGTH: 16
<212> TYPE: PRT
<213> ORGANISM: Artificial Sequence
<220> FEATURE:
<223> OTHER INFORMATION: D form retroinversion peptide
<220> FEATURE:
<221> NAME/KEY: MOD_RES
<222> LOCATION: (1)..(1)
<223> OTHER INFORMATION: dansylated
<220> FEATURE:
<221> NAME/KEY: MISC_FEATURE
<222> LOCATION: (2)..(16)
<223> OTHER INFORMATION: D form amino acid

<400> SEQUENCE: 53

Lys Arg Thr Arg Leu Arg Arg Asn His Ser Ser His Lys Ala Asn Thr
1               5                   10                  15


<210> SEQ ID NO 54
<211> LENGTH: 16
<212> TYPE: PRT
<213> ORGANISM: Artificial Sequence
<220> FEATURE:
<223> OTHER INFORMATION: dansylated membrane translocating peptide
<220> FEATURE:
<221> NAME/KEY: MOD_RES
<222> LOCATION: (1)..(1)
<223> OTHER INFORMATION: dansylated

<400> SEQUENCE: 54

Lys Thr Asn Ala Lys His Ser Ser His Asn Arg Arg Leu Arg Thr Arg
1               5                   10                  15


<210> SEQ ID NO 55
<211> LENGTH: 12
<212> TYPE: PRT
<213> ORGANISM: Artificial Sequence
<220> FEATURE:
<223> OTHER INFORMATION: dansylated cyclic peptide
<220> FEATURE:
<221> NAME/KEY: MOD_RES
<222> LOCATION: (1)..(1)
<223> OTHER INFORMATION: dansylated

<400> SEQUENCE: 55

Lys Lys Thr Asn Ala Lys His Ser Ser His Asn Arg
1               5                   10


<210> SEQ ID NO 56
<211> LENGTH: 16
<212> TYPE: PRT
<213> ORGANISM: Artificial Sequence
<220> FEATURE:
<223> OTHER INFORMATION: dansylated peptide, cyclic internal
<220> FEATURE:
<221> NAME/KEY: MOD_RES
<222> LOCATION: (1)..(1)
<223> OTHER INFORMATION: dansylated

<400> SEQUENCE: 56

Lys Thr Asn Ala Lys His Ser Ser Cys Asn Arg Arg Leu Arg Cys Arg
1               5                   10                  15
```

-continued

```
<210> SEQ ID NO 57
<211> LENGTH: 42
<212> TYPE: PRT
<213> ORGANISM: Artificial Sequence
<220> FEATURE:
<223> OTHER INFORMATION: dansylated peptide
<220> FEATURE:
<221> NAME/KEY: MOD_RES
<222> LOCATION: (1)..(1)
<223> OTHER INFORMATION: dansylated
<220> FEATURE:
<221> NAME/KEY: MOD_RES
<222> LOCATION: (42)..(42)
<223> OTHER INFORMATION: blocked

<400> SEQUENCE: 57

Lys Ser Pro Cys Gly Gly Ser Trp Gly Arg Phe Met Gln Gly Gly Leu
1               5                   10                  15

Phe Gly Gly Arg Thr Asp Gly Cys Gly Ala His Arg Asn Arg Thr Ser
            20                  25                  30

Ala Ser Leu Glu Pro Pro Ser Ser Asp Tyr
        35                  40


<210> SEQ ID NO 58
<211> LENGTH: 14
<212> TYPE: PRT
<213> ORGANISM: Artificial Sequence
<220> FEATURE:
<223> OTHER INFORMATION: membrane translocating peptide, cyclic internal

<400> SEQUENCE: 58

Lys Lys Cys Ala Ala Val Leu Leu Pro Val Leu Leu Ala Cys
1               5                   10


<210> SEQ ID NO 59
<211> LENGTH: 12
<212> TYPE: PRT
<213> ORGANISM: Artificial Sequence
<220> FEATURE:
<223> OTHER INFORMATION: membrane translocating peptide

<400> SEQUENCE: 59

Lys Lys Ala Ala Val Leu Leu Pro Val Leu Leu Ala
1               5                   10
```

MEMBRANE TRANSLOCATING PEPTIDE DRUG DELIVERY SYSTEM

CROSS-REFERENCE TO RELATED APPLICATIONS

This application is a continuation of U.S. application Ser. No. 09/671,089, filed Sep. 27, 2000, now U.S. Pat. No. 6,780,846, which claims the benefit of U.S. Provisional Application No. 60/156,246, filed on Sep. 27, 1999, the disclosures of which are incorporated by reference herein.

FIELD OF THE INVENTION

The present invention relates to peptides, which enhance uptake of a pharmaceutically active agent into a cell, into or out of an intracellular compartment, and across a cell layer. More particularly, the present invention relates to membrane translocating peptides, fragments, motifs, derivatives, analogs or peptidomimetics thereof and to the nucleotide sequences coding therefor, which enhance uptake of a pharmaceutically active agent into a cell, into or out of an intracellular compartment, and across a cell layer either directly or from a pharmaceutically active agent loaded particle.

BACKGROUND OF THE INVENTION

The epithelium lining the gastrointestinal tract (hereinafter, "GIT") is a major barrier to absorption of orally administered pharmaceutically active agents (hereinafter, "active agents"). Absorption across the GIT epithelium can be by transcellular transport through the cells and by paracellular transport between the cells. Transcellular transport includes, but is not limited to, receptor-mediated, transporter-mediated, channel-mediated, pinocytotic and endocytotic mechanisms and to diffusion. Paracellular transport includes, but is not limited to, movement through tight junctions. Of particular interest is the development of non-invasive methods for enhancing uptake of active agents across the GIT epithelium into the body (Evers, P. Developments in Drug Delivery: Technology and Markets, Financial Times Management Report, 1995).

To develop non-invasive methods, phage display libraries have been used to identify specific peptide sequences, which bind preferentially to specific GIT membrane receptor, transporter, channel, pinocytotic or endocytotic target pathways (hereinafter, "targeting peptides") within the GIT. Included among the target pathways, which have been screened with phage display libraries, are the GIT membrane transporters HPT1, hPEPT1, D2H and hSI. HPT1 and hPEPT1 transport dipeptides and tripeptides. D2H transports neutral and basic amino acids and is a transport activating protein for a range of amino acid translocases. hSI is involved in sugar metabolism and comprises 9% of the brush border protein in the jejunum. Specific peptide sequences, which interact with the HPT1, hPEPT1, D2H and hSI membrane transporters have been identified in U.S. patent application Ser. Nos. 09/079,819, 09/079,723 and 09/079,678 (hereby incorporated by reference in their entireties).

Non-target pathway based assays have been used to identify peptides with inherent cell membrane translocating properties. These cell membrane translocating peptides interact directly with and penetrate the lipids of cell membranes (Fong et al. Drug Development Research 33:64, 1994). The central hydrophobic h-region of the signal sequence of Kaposi's fibroblast growth factor, AAVLLPVLLAAP (SEQ ID NO: 1) is considered to be a membrane translocating peptide. This peptide (SEQ ID NO: 1) has been used as a carrier to deliver various short peptides (<25 mer), through the lipid bilayer, into living cells in order to study intracellular protein functions and intracellular processes (Lin et al. J. Biol. Chem. 271:5305, 1996; Liu et al. Proc. Natl. Acad. Sci. USA 93:11819, 1996; Rojas et al. J. Biol. Chem. 271:27456, 1996; Rojas et al. Biochem. Biophys. Res. Commun. 234:675, 1997). A 41-kDa glutathione S-transferase fusion protein containing SEQ ID NO: 1 (GST-Grbs-$SH_2$ fused to SEQ ID NO: 1) has been shown to be imported into NIH 3T3 fibroblasts and to inhibit epidermal growth factor induced EGFR-Grb2 association and MAP kinase activation (Rojas et al. Nature Biotechnology 16:370, 1998). However, these studies do not address the use of membrane translocating peptides to enhance active agent uptake into a cell, into and out of an intracellular compartment, or across a cell layer when the active agent is complexed to a membrane translocating peptide or when the active agent is incorporated into a particle and the particle is modified with (hereinafter, "complexed to") a membrane translocating peptide.

The ability to enhance movement of an active agent across a cell membrane is important because, although an active agent can be administered to an animal by a variety of routes including, but not limited to, oral, nasal, mucosal, topical transdermal, intravenous, intramuscular, intraperitoneal, intrathecal and subcutaneous, oral administration is the preferred route. Nasal, mucosal, topical and transdermal administration depend on drug absorption through the mucosa or skin into the circulation. Intravenous administration can result in adverse effects from rapid accumulation of high concentrations of drug, in patient discomfort and in infection at the injection site. Intramuscular administration can cause pain at the injection site. Subcutaneous administration is not suitable for large volumes or for irritating substances. Although oral administration is the preferred route, many active agents are not absorbed efficiently across the GIT epithelium. This results from enzymatic degradation of active agents within the lumen of the GIT, from the limited permeability of the GIT epithelium to active agents, from the large molecular size of active agents and from the hydrophilic properties of active agents (Fix, J A. J. Pharmac. Sci. 85:1282, 1996). To develop an oral formulation, an active agent must be protected from enzymatic digestion within the lumen of the GIT, presented to the absorptive epithelial cells of the GIT in an effective concentration and "moved" across the epithelium in an apical to basolateral direction.

Therefore, because of the advantages of oral drug administration, there is a need for delivery systems, which protect orally ingested active agents from enzymatic degradation within the lumen of the GIT and which promote the absorption of orally ingested active agents into and across the epithelial cells lining the GIT.

SUMMARY OF THE INVENTION

The present invention fulfills this need by providing a membrane translocating peptide comprising a full-length peptide, derivative, fragment, motif, analog or peptidomimetic thereof (hereinafter, "MTLP") or nucleotide sequences coding therefore, a MTLP-active agent complex and a MTLP-active particle complex, wherein the MTLP enhances movement of the active agent or the active particle across a lipid membrane. More particularly, the present invention provides a MTLP, a MTLP-active agent complex and a MLTP-active particle complex, wherein the MTLP enhances movement of the active agent or of the active particle into a cell, into and out of an intracellular compartment and across a cell layer in an animal, including a human. Methods of making and methods of using MTLPs, MTLP-active agent complexes and MTLP-active particle complexes also are included.

MTLPs of the present invention are capable of displaying one or more known functional activities associated with a full-length MTLP. Such functional activities include, but are not limited to, the ability to interact with a membrane and the ability to compete for transport of a reporter drug molecule (fMLP) across epithelial cells including, but not limited to, polarized, differentiated human derived Caco-2 cells. Additional functional activities include, but are not limited to, antigenicity, which includes, but is not limited to, the ability to bind to an anti-MTLP antibody and the ability to compete with a MTLP for interaction with a membrane; and, immunogenicity, which includes, but is not limited to, the ability to stimulate antibody generation.

Methods of making a MTLP-active agent complex include, but are not limited to, covalent coupling of a MTLP and an active agent and noncovalent coupling of a MTLP and an active agent. Methods of making a MTLP-active particle complex include, but are not limited to, incorporating an active agent into a particle including, but not limited to, a nanoparticle, a microparticle, a capsule, a liposome, a non-viral vector system and a viral vector system. The MTLP can be complexed to the active particle by methods including, but not limited to, adsorption to the active particle, noncovalent coupling to the active particle and covalent coupling, either directly or via a linker, to the active particle, to the polymer or polymers used to synthesize the active particle, to the monomer or monomers used to synthesize the polymer, and to other components comprising the active particle.

The present invention also includes the nucleotide sequences, which code for the MTLPs. Methods of making nucleotide sequences include, but are not limited to, recombinant means.

MTLPs, MTLP-active agent complexes and MTLP-active particle complexes can be used alone, in combination with or conjugated to other molecules including, but not limited to, molecules that bind to target pathways, to nuclear uptake pathways and to endosomal pathways, molecules that enable mucoadhesion, molecules that facilitate diffusion across lipid membranes or through water filled pores and molecules that regulate or direct intra-cellular trafficking. That is, by using different mechanisms simultaneously, active agent bioavailability may be enhanced.

Therefore it is an object of the present invention to provide a full-length MTLP.

Another object of the present invention is to provide fragments, motifs, derivatives, analogs and peptidomimetics of a full-length MTLP.

Another object of the present invention is to provide a composition comprising an MTLP-active agent complex.

Another object of the present invention is to provide a composition comprising an MTLP-active particle complex.

Another object of the present invention is to provide a composition comprising an MTLP-active particle complex, wherein the particle is a microparticle.

Another object of the present invention is to provide a composition comprising an MTLP-active particle complex, wherein the particle is a nanoparticle.

Another object of the present invention is to provide a composition comprising an MTLP-active particle complex, wherein the particle is a liposome.

Another object of the present invention is to provide a composition comprising a viral DNA particle, wherein the viral particle is modified to express a MTLP on its surface.

Another object of the present invention is to provide a composition comprising a viral DNA particle, wherein the viral particle is complexed to a MLTP following virus production and purification.

Another object of the present invention is to provide a composition comprising a viral DNA particle, wherein the viral particle is complexed to a MTLP following virus production in and purification from a mammalian cell.

Another object of the present invention is to provide a composition comprising a non-viral based gene delivery system, wherein the non-viral based gene delivery system is complexed to a MTLP.

Another object of the present invention is to enhance the movement of an active agent across a lipid membrane.

Another object of the present invention is to enhance the uptake of an active agent into a cell.

Another object of the present invention is to enhance the uptake of an active agent across a cell layer.

Another object of the present invention is to enhance the uptake of an active agent into an epithelial cell.

Another object of the present invention is to enhance the uptake of an active agent across an epithelial cell layer.

Another object of the present invention is to enhance the uptake of an active agent across the epithelial cell layer lining the GIT into the circulation of an animal.

Another object of the present invention is to enhance the movement of an active particle across a lipid membrane.

Another object of the present invention is to enhance the uptake of an active particle into a cell.

Another object of the present invention is to enhance the uptake of an active particle across a cell layer.

Another object of the present invention is to enhance the uptake of an active particle into an epithelial cell.

Another object of the present invention is to enhance the uptake of an active particle across an epithelial cell layer.

Another object of the present invention is to enhance the uptake of an active particle across the epithelial cell layer lining the GIT into the circulation of an animal.

Another object of the present invention is to provide intracellular gene delivery by a non-viral based gene delivery system.

Another object of the present invention is to provide intracellular gene delivery by a non-viral based gene delivery system, wherein the non-viral based gene delivery system is complexed to a MTLP.

Another object of the present invention is to provide a rapid screening method to identify MTLPs, which retain the essential functional activity of the full-length MTLP.

Another object of the present invention is to provide cell-based screens for assaying the functional activity of a MTLP.

Another object of the present invention is to provide cell-based screens for characterizing the properties of a MTLP.

Another object of the present invention is to provide a method for diagnosing a pathological disorder by oral administration of an amount of a MTLP-active agent complex, wherein the active agent is a diagnostic agent, such that the systemic concentration of the diagnostic agent is effective to diagnose the pathological disorder.

Another object of the present invention is to provide a method for preventing a pathological disorder by oral administration of a MTLP-active agent complex, wherein the active agent is a prophylactic agent, such that the systemic concentration of the prophylactic agent is effective to prevent the pathological disorder.

Another object of the present invention is to provide a method for treating a pathological disorder by oral administration of a MTLP-active agent complex, wherein the active agent is a therapeutic agent, such that the systemic concentration of the therapeutic agent is effective to treat the pathological disorder.

Another object of the present invention is to provide a method for diagnosing a pathological disorder by oral administration of a MTLP-active particle complex, wherein the active particle contains a diagnostic agent, such that the systemic concentration of the diagnostic agent is effective to diagnose the pathological disorder.

Another object of the present invention is to provide a method for preventing a pathological disorder by oral administration of a MTLP-active particle complex, wherein the active particle contains a prophylactic agent, such that the systemic concentration of the prophylactic agent is effective to prevent the pathological disorder.

Another object of the present invention is to provide a method for treating a pathological disorder by oral administration of a MTLP-active particle complex, wherein the active particle contains a therapeutic agent such that the systemic concentration of the therapeutic agent is effective to treat the pathological disorder.

Other objectives, features and advantages of the present invention will become apparent after a review of the following detailed description of the disclosed embodiments and the appended claims.

DETAILED DESCRIPTION OF THE INVENTION

Figure 1:
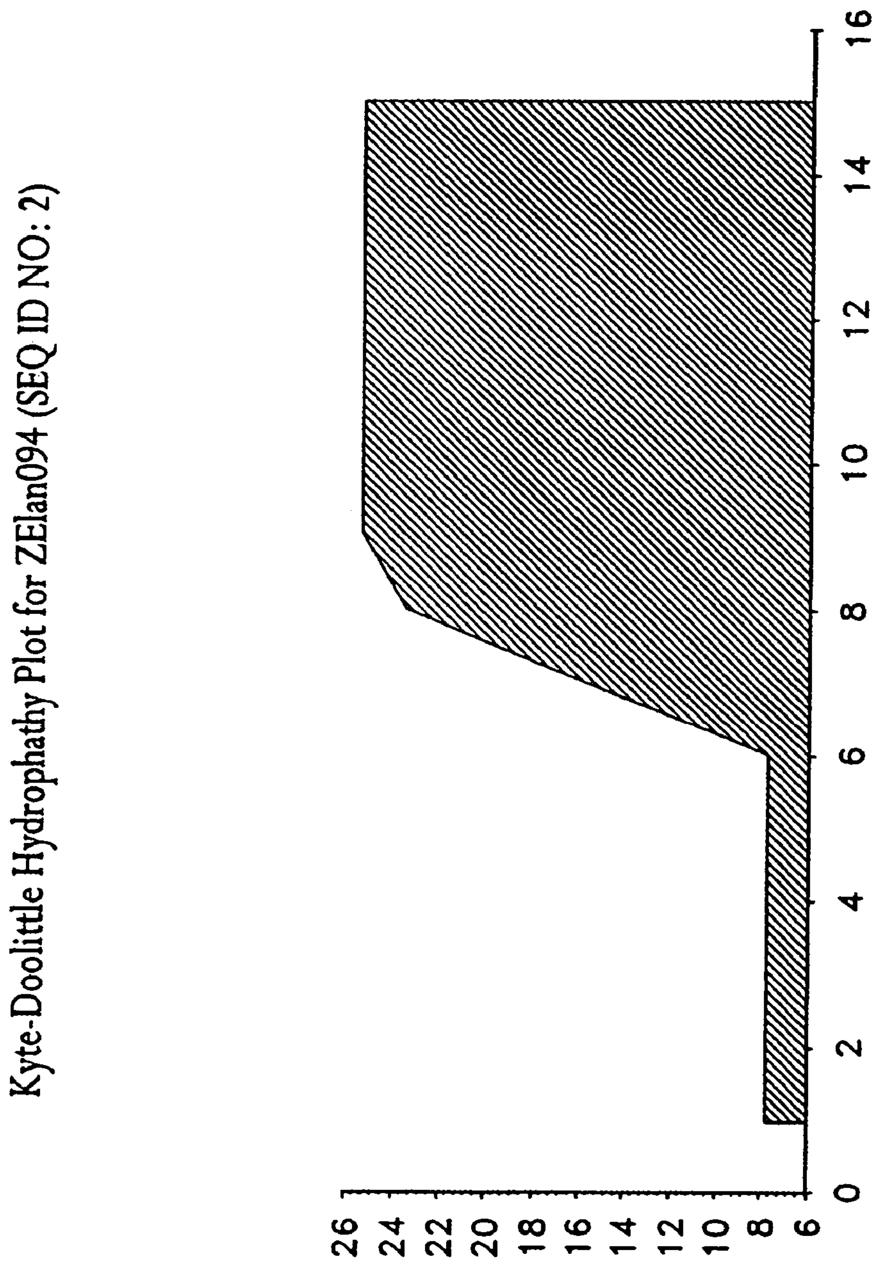
FIG. 1 shows the hydropathy plot for ZElan094 (15 mer) (SEQ ID NO: 2)

The present invention relates to novel membrane translocating peptides, comprising a full-length peptide, derivative, fragment, motif, analog or peptidomimetic thereof (MTLPs), to nucleotide sequences coding therefor, to MTLP-active agent complexes and to MTLP-active particle complexes, wherein the MTLP enhances movement of the active agent or of the active particle across a membrane. More particularly, the present invention relates to novel MTLPs, to nucleotide sequences coding therefore, to MTLP-active agent complexes and to MTLP-active particle complexes, wherein the MTLP enhances movement of the active agent in the MTLP-active agent complex, of the active agent in the MTLP-active particle complex and of the active particle in the MTLP active-particle complex into a cell, into and out of an intracellular compartment and across a cell layer in an animal, including a human. Methods of making and methods of using MTLPs also are included.

The present invention also provides methods for diagnosing, preventing or treating a pathological disorder in an animal in need of diagnosis, prevention or treatment of a pathological disorder by administrating to the animal an amount of a MTLP-active agent complex or of a MTLP-active particle complex, such that the systemic concentration of the active agent is effective to diagnose, prevent or treat the pathological disorder.

An "active agent", as used herein, includes any diagnostic, prophylactic or therapeutic agent that can be used in an animal, including a human.

An "active particle", as used herein is a particle into which one or more active agents have been loaded.

A membrane translocating peptide, as used herein, is a peptide which interacts directly with and penetrates the lipids of a physiological membrane.

A "MTLP", as used herein, is a full-length membrane translocating peptide or a derivative, fragment, motif, analog and peptidomimetic thereof, which displays one or more motifs of the full-length peptide and one or more of the functional activities of the full-length peptide.

"Complexed to", as used herein, includes adsorption, non-covalent coupling and covalent coupling of a MTLP to an active agent or to an active particle.

A "MTLP-active agent complex", as used herein, includes one or more MTLPs complexed to an active agent.

A "MTLP-active particle complex", as used herein, includes one or more MTLPs complexed to an active particle.

The active agent used depends on the pathological condition to be diagnosed, prevented or treated, the individual to whom it is to be administered, and the route of administration. Active agents include, but are not limited to, imaging agents, antigens, antibodies, oligonucleotides, antisense oligonucleotides, genes, gene correcting hybrid oligonucleotides, aptameric oligonucleotides, triple-helix forming oligonucleotides, ribozymes, signal transduction pathway inhibitors, tyrosine kinase inhibitors, DNA-modifying agents, therapeutic genes, systems for therapeutic gene delivery, drugs and other agents including, but not limited to, those listed in the United States Pharmacopeia and in other known pharmacopeias Drugs include, but are not limited to, peptides, proteins, hormones and analgesics, cardiovascular, narcotic, antagonist, chelating, chemotherapeutic, sedative, anti-hypertensive, anti-anginal, anti-migraine, anti-coagulant, anti-emetic anti-neoplastic and anti-diuretic agents Hormones include, but are not limited to, insulin, calcitonin, calcitonin gene regulating protein, atrial natriuretic protein, colony stimulating factor, erythropoietin (EPO), interferons, somatotropin, somatostatin, somatomedin, luteinizing hormone releasing hormone (LHRH), tissue plasminogen activator (TPA), growth hormone releasing hormone (GHRH), oxytocin, estradiol, growth hormones, leuprolide acetate, factor VIII, testosterone and analogs thereof. Analgesics include, but are not limited to, fentanyl, sufentanil, butorphanol, buprenorphine, levorphanol, morphine, hydromorphone, hydrocodeine, oxymorphone, methadone, lidocaine, bupivacaine, diclofenac, naproxen, paverin, and analogs thereof. Anti-migraine agents include, but are not limited to heparin, hirudin, and analogs thereof. Anti-coagulant agents include, but are not limited to, scopolamine, ondansetron, domperidone, etoclopramide, and analogs thereof. Cardiovascular, anti-hypertensive and vasodilator agents include, but are not limited to, diltiazem, clonidine, nifedipine, verapamil, isosorbide-5-mononitrate, organic nitrates, nitroglycerine and analogs thereof. Sedatives include, but are not limited to, benzodiazeines, phenothiozines and analogs thereof. Narcotic antagonists include, but are not limited to, naltrexone, naloxone and analogs thereof. Chelating agents include, but are not limited to deferoxamine and analogs thereof. Anti-diuretic agents include, but are not limited to, desmopressin, vasopressin and analogs thereof. Anti-neoplastic agents include, but are not limited to, 5-fluorouracil, bleomycin, vincristine, procarbazine, temezolamide, CCNU, 6-thioguanine, hydroxyurea and analogs thereof.

An active agent can be formulated in neutral or salt form. Pharmaceutically acceptable salts include, but are not limited to, those formed with free amino groups; those formed with free carboxyl groups; and, those derived from sodium, potassium, ammonium, calcium, ferric hydroxide, isopropylamine, triethylamine, 2-ethylaminoethanol, histidine and procaine. An active agent can be loaded into a particle prepared from pharmaceutically acceptable ingredients including, but not limited to, soluble, insoluble, permeable, impermeable, biodegradable or gastroretentive polymers or liposomes. Such particles include, but are not limited to, nanoparticles, biodegradable nanoparticles, microparticles, biodegradable microparticles, nanospheres, biodegradable nanospheres, microspheres, biodegradable microspheres, capsules, emulsions, liposomes, micelles and viral vector systems.

MTLPs for use in the present invention include fill-length peptides, derivatives, fragments, motifs, analogs and peptidomimetics thereof, which display one or more motifs of the fill-length peptide and one or more functional activities of the full-length peptide. Such functional activities include, but are not limited to, enhancing uptake of an active agent into a cell, into and out of an intracellular compartment and across a cell layer and competing with the full-length peptide in enhancing uptake of an active agent into a cell, across a cell layer or into and out of an intracellular compartment.

Such MTLPs include, but are not limited, to those containing as primary amino acid sequences, all or part of the amino acid sequences substantially as depicted in Table 1

TABLE 1

MTLPs Amino acid sequences

| SEQUENCE | ZELAN NO. | SEOUENCE ID NO. |
|---|---|---|
| KKAAAVLLPVLLAAPFITC-LC | 094 | 2 |
| KKKAAAVLLPVLLAAP | Felan094 | 3 |
| KKAAAVLLPVLLAAPREDL | 094R | 4 |
| KKCAAVLLPVLLAAPC | 176 | 5 |
| CAAVLLPVLLAAC | 177 | 6 |
| KKCAAVLLPVLLAC | 178 | 7 |
| CAAVLLPVLLC | 179 | 8 |

TABLE 1-continued

MTLPs Amino acid sequences

| SEQUENCE | ZELAN NO. | SEOUENCE ID NO. |
|---|---|---|
| CAAVLLPVLC | 180 | 9 |
| CAVLLPVLLAAPC | 181 | 10 |
| CVLLPVLLAAPC | 182 | 11 |
| CLLPVLLAAPC | 183 | 12 |
| CLPVLLAAPC | 184 | 13 |
| AAVLLPVLLAAP | 185 | 14 |
| AAVLLPVLLAA | 186 | 15 |
| KKAAVLLPVLLA | 187 | 16 |
| AAVLLPVLL | 188 | 17 |
| AAVLLPVL | 189 | 18 |
| AVLLPVLLAAP | 190 | 19 |
| VLLPVLLAAP | 191 | 20 |
| LLPVLLAAP | 192 | 21 |
| LPVLLAAP | 193 | 22 |
| AAVLLPVLLAAKKKRKA | 204N | 23 |
| KKKRKAAAAVLLPVLLA | 204 | 24 |

[Underline denotes cyclisation]

The 15 residue hydrophobic peptide ZElan094 (SEQ ID NO: 2) is related in sequence to the 12 residue hydrophobic peptide sequence AAVLLPVLLAAP (SEQ ID NO: 1) (Rojas et al. Nature Biotechnology 16:370, 1998). However, the 15 residue ZElan094 differs from the 12 residue SEQ ID NO: 1 in that it has three additional amino acid residues, KKA, at the N-terminus and a blocking amide at the C-terminus. These N-terminus and C-terminus modifications are designed to enhance the solubility and the in vivo stability of the MTLP, respectively. The $NH_2$ terminus alanine also may contribute to the alpha helical properties of the peptide.

The MTLPs of the present invention include peptides comprising all of or a fragment of ZElan094 or having at least 4 of the contiguous amino acids of ZElan094. The MTLPs of the present invention also include sequences that are substantially homologous to regions of ZElan094. Preferably these show at least 40%, 50%, 60%, 70%, 80% or 90% identity over an identical size sequence or when compared to an aligned sequence in which the alignment is done by a computer homology program known in the art. Moreover, the encoding nucleic acids of the MTLPs should be capable of hybridizing to a coding sequence of ZElan094 under stringent, moderately stringent or non-stringent conditions.

MTLPs also include, but are not limited to, peptides in which certain amino acid residues are added or deleted or in which certain amino acid residues are replaced or substituted by other amino acid residues of similar properties, which provide for functionally equivalent molecules. For example, an amino acid residue can be substituted by another amino acid residue or analogue thereof of similar polarity, which acts as a functional equivalent and results in a silent change.

A substitution for an amino acid within a sequence may be selected from other members of the class to which the amino acid belongs. The nonpolar (hydrophobic) amino acids include alanine, leucine, isoleucine, valine, proline, phenylalanine, tryptophan and methionine. The neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Additionally, any residue can be replaced by a natural residue, which enhances solubility, in vivo stability, interaction with a lipid membrane or uptake across a lipid membrane.

Moreover, if desired, a nonclassical amino acid or a chemical amino acid analog can be introduced as a substitution or addition into a MTLP. Non-classical amino acids include, but are not limited to, the D-isomers of the common amino acids, alpha amino-isobutyric acids, amino-butyric acids, amino-hexanoic acids, amino-propionic acids, ornithine, norleucine, norvaline, hydroxyproline, sarcosine, citrulline, cysteic acid, t-butylglycine, t-butylguanine, phenylglycine, cyclohexyl-alanine, P-alanine, fluoro-amino acids and designer amino acids such as, but not limited to, P-methyl, Ca-methyl and Na-methyl amino acids and amino acid analogs. Any residue can be replaced by a nonclassical or a chemical amino acid, which enhances solubility, in vivo stability, interaction with a lipid membrane or uptake across a lipid membrane.

Nucleic acid sequences, which encode the peptide sequences of the MTLPs ZElan094, Felan 094, ZElan 094R, 176-193, 204N and 204 (SEQ ID NOS: 2-24) are provided in Table 2 (SEQ ID NOS: 25-47). However, due to the degeneracy of nucleotide coding sequences, different nucleotide sequences, which encode substantially the same amino acid sequence, may be used. That is, a nucleotide sequence, altered by substitution of a different codon, can encode a functionally equivalent amino acid to produce a silent change.

MTLPs may be synthesized using chemical methods (U.S. Pat. Nos. 4,244,946, 4,305,872 and 4,316,891; Merrifield et al. J. Am. Chem. Soc. 85:2149, 1964; Vale et al. Science 213:1394, 1981; Marki et al. J. Am. Chem. Soc. 103:3178, 1981); recombinant DNA methods (Maniatis, Molecular Cloning, a Laboratory Manual, 2d ed. Cold Spring Harbor Laboratory, Cold Spring Harbor N.Y., 1990); viral expression or other methods known to those skilled in the art.

Chemical methods include, but are not limited to, solid phase peptide synthesis. Briefly, solid phase peptide synthesis consists of coupling the carboxyl group of the C-terminal amino acid to a resin and successively adding N-alpha protected amino acids. The protecting groups may be any known in the art. Before an amino acid is added to the growing peptide chain, the protecting group of the previous amino acid is removed (Merrifield J. Am. Chem. Soc. 85:2149 1964; Vale et al. Science 213:1394, 1981; Marki et al. J. Am. Chem. Soc. 103:3178, 1981). The synthesized peptides are then purified by methods known in the art.

TABLE 2

MTLPs nucleic acid sequence

| SEQ ID NO: | ZElan NO: | SEQUENCE |
|---|---|---|
| 25 | 94 | AARAARGCNGCNGCNGTNYTNYTNCCNGTNYTNYTNGCNGCNCCN |
| 26 | Felan 094 | YTNTGYAARAARAARGCNGCNGCNGTNYTNYTNCCNGTNYTNYTN-GCNGCNCCN |
| 27 | 094R | AARAARGCNGCNGCNGTNYTNYTNCCNGTNYTNYTNGCNGCNCC-NMGNGARGAYYTN |
| 28 | 176 | AARAARTGYGCNGCNGTNYTNYTNCCNGTNYTNYTNGCNGCNCCNTGY |
| 29 | 177 | TGYGCNGCNGTNYTNYTNCCNGTNYTNYTNGCNGCNTGY |
| 30 | 178 | TGYGCNGCNGTNYTNYTNCCNGTNYTNYTNGCNTGY |
| 31 | 179 | TGYGCNGCNGTNYTNYTNCCNGTNYTNYTNTGY |
| 32 | 180 | TGYGCNGCNGTNYTNYTNCCNGTNYTNTGY |
| 33 | 181 | TGYGCNGTNYTNYTNCCNGTNYTNYTNGCNGCNCCNTGY |
| 34 | 182 | TGYGTNYTNYTNCCNGTNYTNYTNGCNGCNCCNTGY |
| 35 | 183 | TGYYTNYTNCCNGTNYTNYTNGCNGCNCCNTGY |
| 36 | 184 | TGYYTNCCNGTNYTNYTNGCNGCNCCNTGY |
| 37 | 185 | GCNGCNGTNYTNYTNCCNGTNYTNYTNGCNGCNCCN |
| 38 | 186 | GCNGCNGTNYTNYTNCCNGTNYTNYTNGCNGCN |
| 39 | 187 | AARAARGCNGCNGTNYTNYTNCCNGTNYTNYTNGCN |
| 40 | 188 | GCNGCNGTNYTNYTNCCNGTNYTNYTN |

TABLE 2-continued

MTLPs nucleic acid sequence

| SEQ ID NO: | ZElan NO: | SEQUENCE |
|---|---|---|
| 41 | 189 | GCNGCNGTNYTNYTNCCNGTNYTNYTN |
| 42 | 190 | GCNGTNYTNYTNCCNGTNYTNYTNGCNGCNCCN |
| 43 | 191 | GTNYTNYTNCCNGTNYTNYTNGCNGCNCCN |
| 44 | 192 | YTNYTNCCNGTNYTNYTNGCNGCNCCN |
| 45 | 193 | YTNCCNGTNYTNYTNGCNGCNCCN |
| 46 | 204N | CNGCNGTNYTNYTNCCNGTNYTNYTNGCNGCNAARAARAARMGNA-ARGCN |
| 47 | 204 | AARAARAARMGNAARGCNGCNGCNGCNGTNYTNYTNCCNGTNYTNY-TNGCN |

Preferably, solid phase peptide synthesis is done using an automated peptide synthesizer such as, but not limited to, an Applied Biosystems Inc. (ABI) model 431A using the "Fastmoc" synthesis protocol supplied by ABI. This protocol uses 2-(1H-Benzotriazol-1-yl)-1,1,3,3-tetramethyluronium hexafluorophosphate (HBTU) as coupling agent (Knorr et al. Tet. Lett. 30:1927, 1989). Syntheses can be carried out on 0.25 mmol of commercially available 4-(2',4'-dimethoxyphenyl-(9-fluorenyl-ethoxycarbonyl)-aminomethyl) phenoxy polystyrene resin (Rink H. Tet. Lett. 28:3787, 1987). Fmoc amino acids (1 mmol) are coupled according to the Fastmoc protocol. N-methylpyrrolidone (NMP) is used as solvent, with HBTU dissolved in N,N-dimethylformamide (DMF). The following side chain protected Fmoc amino acid derivatives are used: FmocArg(Pmc)OH; FmocAsn (Mbh)OH; FmocAsp(tBu)OH; FmocCys(Acm)OH; FmocGlu(tBu)OH; FmocGln(Mbh)OH; FmocHis(Tr)OH; FmocLys(Boc)OH; FmocSer-(tBu)OH; FmocThr(tBu)OH; FmocTyr(tBu)OH. (Abbreviations: Acm:acetamidomethyl; Boc:tert-butoxycarbonyl; tBu:tert-butyl; Fmoc:9-fluorenylmethoxy-carbonyl; Mbh:4,4'-dimethoxybenzhydryl; Pmc:2,2,5,7,8-pentamethyl-chro-man-6-sulfonyl; Tr:5 trityl.)

At the end of each synthesis, the amount of peptide is assayed by ultraviolet spectroscopy. A sample of dry peptide resin (about 3-10 mg) is weighed, then 20% piperidine in DMA (10 ml) is added. After 30 min sonication, the UV (ultraviolet) absorbance of the dibenzofulvene-piperidine adduct (formed by cleavage of the N-terminal Fmoc group) is recorded at 301 nm. Peptide substitution (in mmol/g) is calculated according to the equation:

$$\text{Substitution} = \frac{A \times v \times 1000}{7800 \times w}$$

where A is the absorbance at 301 nm, v the ml of 20% piperidine in DMA, 7800 the extinction coefficient (mol/dm$^3$/cm) of the dibenzofulvene-piperidine adduct, and w the mg of peptide resin sample. The N-terminal Fmoc group is cleaved using 20% piperidine in DMA, then acetylated using acetic anhydride and pyridine in DMA. The peptide resin is thoroughly washed with DMA, $CH_2C_{12}$ and diethyl ether.

Methods used for cleavage and deprotection (King et al. Int. J. Peptide Protein Res. 36:255, 1990) include, but are not limited to, treating the air-dried peptide resin with ethylmethyl-sulfide (EtSMe), ethanedithiol (EDT) and thioanisole (PhSMe) for approximately 20 min and adding 95% aqueous trifluoracetic acid (TFA). Approximately 50 ml of these reagents are used per gram of peptide resin in a ratio of TFA:EtSMe:EDT:PhSme (10:0.5:0.5:0.5). The mixture is stirred for 3 h at RT under an $N_2$ atmosphere, filtered and washed with TFA (2×3 ml). The combined filtrate is evaporated in vacuo and anhydrous diethyl ether is added to the yellow/orange residue. The resulting white precipitate is isolated by filtration. Purification of the synthesized peptides is done by standard methods including, but not limited to, ion exchange, affinity, sizing column and high performance liquid chromatography, centrifugation or differential solubility.

Recombinant DNA methods for expressing peptides are well known to those skilled in the art and include expression in a biological system including, but not limited to a mammalian system, an insect system, a plant system and a viral system (Maniatis, T. Molecular Cloning, A Laboratory Manual, 2d ed., Cold Spring Harbor Laboratory, Cold Spring Harbor, N.Y., 1990). For example, a MTLP can be expressed by a virus, by a virus fused to a viral coat protein, a viral capsid protein or a viral surface protein. Further, MTLP-viral protein complexes can be expressed in mammalian hosts or in helper viruses used to produce the virus of interest.

In the production of a gene encoding a derivative, fragment, motif, analog or peptidomimetic of a full-length peptide, care should be taken to ensure that the modified gene remains within the same translational reading frame uninterrupted by translational stop signals in the gene region where the desired activity is encoded.

The cloned MTLP gene sequence can be modified by any of numerous strategies known in the art (Maniatis, T. Molecular Cloning, A Laboratory Manual, 2d ed., Cold Spring Harbor Laboratory, Cold Spring Harbor, N.Y., 1990). The sequence can be cleaved at appropriate sites with restriction endonuclease(s), enzymatically modified, isolated, and ligated in vitro. A nucleic acid can be mutated in vitro or in vivo to create and/or to destroy translation, initiation and/or termination sequences, or to create variations in coding regions and/or to form new restriction endonuclease sites or to destroy preexisting ones to facilitate further in vitro modification. Any technique for mutagenesis known in the art can be used including, but not limited to, chemical mutagenesis, in vitro site directed mutagenesis (Hutchinson et al J. Biol Chem 253:6551,1978), TAB® linkers (Amersham Pharmacia, Piscataway, N.J.) and PCR primers containing mutations.

Further, phage display vectors including, but not limited to, bacteriophage M13 or bacteriophage Fd can be modified to express a MTLP fused to the gene III protein product or gene VII protein product of the bacteriophage. A library of sequences coding for MTLP derivatives including, but not limited to, alanine scan positional mutants, successive random positional scanning mutants and sequences derived therefrom as, for example, those shown in Table 1, can be cloned in-frame to either gene III or gene VII of the bacteriophage. The phage display library can then be screened to identify MTLP derivatives having enhanced ability to transport active agents or active particles across membranes.

MTLPs can be modified either during or after chemical or biotechnological synthesis by methods including, but not limited to, glycosylation, acetylation, phosphorylation, amidation, palymitoylation, myristolylation, isoprenylation, lipidaton, alkylation, derivatization, addition of protecting/blocking groups, proteolytic cleavage and linkage to an antibody or other cellular ligand. MTLPs also may be modified by methods including, but not limited to, chemical cleavage by cyanogen bromide, trypsin, chymotrypsin, papain, V8 protease, NaBH, acetylation, formylation, oxidation, reduction, by metabolic synthesis in the presence of tunicamycin or by other methods known in the art.

A derivative form of a MTLP can be a chimeric or fusion peptide, comprising a MTLP or multiple repeats thereof, preferably consisting of at least one domain or motif of the full-length peptide sequence or a portion thereof joined at its amino-terminus, at its carboxy-terminus or at an internal site via a peptide bond to an amino acid sequence of a different peptide. Methods for producing chimeric peptides include, but are not limited to, recombinant expression of a nucleic acid including the MTLP coding sequence joined in-frame to the coding sequence of a different peptide. Using methods known in the art, the nucleic acid sequences encoding the desired amino acid sequences are ligated to each other in the proper order and the chimeric product is expressed. For example, chimeric genes comprising portions of MTLP nucleic acid fused to any heterologous protein-encoding nucleic acid may be constructed. Alternatively, chimeric MTLPs may be synthesized using techniques including, but not limited to, a peptide synthesizer.

MTLPs may be linked to other molecules including, but not limited to, detectable labels, adsorption facilitating molecules, toxins or solid substrata by methods including, but not limited to, the use of homobifunctional and heterobifunctional cross-linking molecules (Carlsson et al. Biochem. J. 173:723, 1978; Cumber et al. Methods in Enzymology 112:207, 1978; Jue et al. Biochem. 17:5399, 1978; Sun et al. Biochem. 13:2334,1974; Blattler et al. Biochem. 24:1517, 1985; Liu et al. Biochem. 18:690, 1979; Youle and Neville Proc. Natl. Acad. Sci. USA 77:5483, 1980; Lerner et al. Proc. Natl. Acad. Sci. USA 78:3403. 1981; Jung and Moroi Biochem. Biophys. Acta 761:162 1983; Caulfield et al. Biochem. 81:7772, 1984; Staros Biochem. 21:3950, 1982; Yoshitake et al. Eur. J. Biochem. 101:395, 1979; Yoshitake et al. J. Biochem. 92:1413,1982; Pilch and Czech J. Biol. Chem. 254:3375,1979; Novick et al. J. Biol. Chem. 262: 8483. 1987; Lomant and Fairbanks J. Mol. Biol. 104:243, 1976; Hamada and Tsuruo Anal. Biochem. 160:483, 1987; Hashida et al J. Applied Biochem. 6:56, 1984; Means and Feeney Bioconjugate Chem. 1:2, 1990).

MTLPs may be used as immunogens to generate antibodies which immunospecifically bind the immunogen. Such antibodies include, but are not limited to polyclonal, monoclonal, chimeric, single chain Fab fragments, $F(ab')_2$ fragments and Fab expression libraries. Uses of such antibodies include, but are not limited to, localization, imaging, diagnosis, treatment and treatment efficacy monitoring. For example, antibodies or antibody fragments specific to a domain of a MTLP, such as a dansyl group or some other epitope introduced into the peptide, can be used to identify the presence of the MTLP, to bind the MTLP to the surface of a particle, to quantitate the amount of the MTLP on a particle, to measure the amount of the MTLP in a physiological sample, to immunocytochemically localize the MTLP in a cell or tissue sample, to image the MTLP after in vivo administration and to purify the MTLP by immunoaffinity column chromatography.

The functional activity of a MTLP can be determined by suitable in vivo or in vitro assays known to those skilled in the art. These include, but are not limited to, immuno-, immunoradiometric-, immunodiffusion- and immunofluorescence assays and to western blot analysis.

A MTLP functions to target an active agent or an active particle to a cell, intracellular compartment, or cell layer and to enhance the uptake of the active agent or of the active particle into a cell, into and out of an intracellular compartment and across a cell layer. Cells include, but are not limited to, epithelial, endothelial and mesothelial cells, unicellular organisms and plant cells. Cell layers include epithelial, endothelial and mesothelial cell layers such as, but not limited to, the gastrointestinal tract, pulmonary epithelium, blood brain barrier and vascular endothelium. Preferably the cell is an epithelial cell and the cell layer is an epithelial cell layer. Most preferably, the cell is a GIT epithelial cell and the cell layer is the GIT epithelial cell layer. Intracellular compartments include, but not limited to, nuclear, mitochondrial, endoplasmic reticular and endosomal compartments. MTLPs can be used to enhance the uptake of an active agent or active particle that regulates or directs intra-cellular trafficking. Further, MTLPs can be used to enhance intracellular gene delivery. That is, a gene or plasmid DNA is encapsulated or complexed within a cationic lipid polymer system and the surface of the cationic lipid polymer system is complexed with an MTLP or with a targeting peptide. Alternatively, a plasmid DNA is condensed, the condensate is complexed with cationic lipids and the surface of the cationic lipids is complexed with an MTLP or with a targeting peptide.

Methods used to complex a MTLP to an active agent (MTLP-active agent complex) include, but are not limited to, covalent coupling of a MTLP and an active agent, either directly or via a lining moiety, noncovalent coupling of a MTLP and an active agent and generation of a fusion protein, wherein a MTLP is fused in-frame to an active agent including, but not limited to a therapeutic protein.

Methods used to complex a MTLP to an active agent loaded particle (MTLP-active particle complex) include, but are not limited to, adsorption to the active particle, noncovalent coupling to the active particle; covalent coupling, either directly or via a linker, to the active particle, to the polymer or polymers used to synthesize the active particle, to the monomer or monomers used to synthesize the polymer, and, to any other component comprising the active particle. Further, MTLPs can be complexed to a slow-release (controlled release) particle or device (Medical Applications of Controlled Release, Langer & Wise (eds.), CRC Press, Boca Raton, Fla., 1974; Controlled Drug Bioavailability, Drug Product Design and Performance, Smolen and Ball (eds.), Wiley, New York, 1984; Ranger et al. J. Macromol. Sci. Rev. Macromol. Chem. 23:61, 1983; Levy et al. Science 228:190, 1985; During et al. Ann. Neurol. 25:351, 1989; Howard et al. J. Neurosurg. 71:105 1989).

Methods used for viral based gene delivery systems include, but are not limited to, vectors modified at the nucleic acid level to express a MTLP on the surface of a viral particle and mammalian cells or helper viruses, which express MTLP-virus fusion proteins that are incorporated into a viral vector.

The present invention also provides pharmaceutical formulations, comprising a therapeutically effective amount of a MTLP-active agent complex or of a MTLP-active particle complex and a pharmaceutically acceptable carrier (Remington's Pharmaceutical Sciences by E. W. Martin). The term "pharmaceutically acceptable" includes, but is not limited to, carriers approved by a regulatory agency of a country or a state government or listed in the U.S. Pharmacopeia or other generally recognized pharmacopeia for use in animals, and more particularly in humans. The term "carrier" refers to a diluent, adjuvant, excipient, or vehicle with which the MTLP-active agent complex or the MTLP-active particle complex is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical formulation is administered orally. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The formulation, if desired, can also contain minor amounts of wetting or emulsifying agents, or pH buffering agents. These compositions include, but are not limited to, solutions, suspensions, emulsion, tablets, pills, capsules, powders and sustained-release formulations. The formulation can be a suppository, with traditional binders and carriers such as triglycerides. Oral formulation can include standard carriers including, but not limited to, pharmaceutical grades of mannitol, lactose, starch, magnesium stearate, sodium saccharine, cellulose and magnesium carbonate. Such formulations will contain a therapeutically effective amount of the active agent or of the active agent loaded into a particle, together with a suitable amount of carrier so as to provide the form for proper administration to an individual in need of the active agent.

Any route known in the art may be used to administer a MTLP-active agent complex or a MTLP-active particle complex, including but not limited, to oral, nasal, topical, mucosal, intravenous, intraperitoneal, intradermal, intrathecal, intramuscular, transdermal and osmotic. Preferably, administration is oral, wherein the MTLP enhances uptake of the active agent into a GIT epithelial cell and across the GIT epithelium into the circulation. The precise amount of active agent to be administered for the diagnosis, prevention or treatment of a particular pathological condition will depend on the pathological disorder, the severity of the pathological disorder, the active agent used and the route of administration. The amount of active agent to be administered and the schedule of administration can be determined by the practitioner using standard clinical techniques. In addition, in vitro assays may optionally be employed to help identify optimal ranges for active agent administration.

The following examples will serve to further illustrate the present invention without, at the same time, however, constituting any limitation thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE 1

Peptide Synthesis

The membrane translocating peptides ZElan094, 204N and 204 and the targeting peptides HAX42, PAX2, P31 and Sni34 (U.S. patent applications Ser. Nos. 09/079,819, 09/079,723 and 09/079,678) were synthesized chemically using a fmoc synthesis protocol (Anaspec, Inc., San Jose, Calif.). A dansyl group was added at the N-terminus of each sequence in order to enable the detection of the peptide with anti-dansyl antibody (Table 3).

TABLE 3

MTLPs and targeting peptide sequences

| SEQUENCE | PEPTIDE | ZELAN NO: | RECEPTOR | SEQ ID NO: |
|---|---|---|---|---|
| $H_2N$-K(dns)KKAAAVLLPVLLAAP MTLP-amide | MTLP | 094 | | 48 |
| AAVLLPVLLAAKKKRKA | MTLP | 204N | | 23 |
| KKKRKAAAAVLLPVLLA | MTLP | 204 | | 24 |
| $H_2N$-K(dns)SDHALGTNLRSDNAK-EPGDYNCCGNGNSTGRKVFNRRRSAIPY | HAX42 | 011 | HPT1 | 49 |
| $H_2N$-K(dns)PGDYNCCGNGNSTG | HAX42 | 091 | HPT1 | 50 |

TABLE 3-continued

| MTLPs and targeting peptide sequences | | | | |
|---|---|---|---|---|
| SEQUENCE | PEPTIDE | ZELAN NO: | RECEPTOR | SEQ ID NO: |
| (14 mer) | | | | |
| $H_2$N-K(dns)LSTPPSREAYSRPYSV-DSDSDTNAKHSSHNRRLRTRSRPN | PAX2 | 055 | HPT1 | 51 |
| $H_2$N-K(dns)Lys-TrKSSrSNPrGrrHPG (15 mer cyclic D form) | P31 | 101 | | 52 |
| $H_2$N-K(dns)rtrlrrnhsshkant (15 mer D form retroinversion) | PAX2 | 144 | RPT1 | 53 |
| $H_2$N-K(dns)TNAKHSSHNRRLRTR | PAX2 | 129 | HPT1 | 54 |
| $H_2$N-K(dns)Lys-TNAKHSSHNR (10 mer cyclic D form) | PAX2 | 128 | HPT1 | 55 |
| $H_2$N-K(dns)TNAKHSSCNRRLRCR (15mer cyclic internal) | PAX2 | 104 | HPT1 | 56 |
| $H_2$N-K(dns)SPCGGSWGRFMQGGL FGGRTDGCGAHRNRTSASLEPPS SDY-$CONH_2$ | Sni34 | 022 | | 57 |

The physical characteristics of ZElan094 (SEQ ID NO: 2) are shown in Table 4.

TABLE 4

| Physical characteristics of ZElan 094 (SEQ ID NO: 2) | |
|---|---|
| Mass (M + H+): | 1838.03 |
| Solubility | 1 mg/ml water |
| Appearance | white powder |
| HPLC purity | >95% |
| Kyle-Doolittle Hydropathy Plot | FIG. 1 |

EXAMPLE 2

Preparation of MTLP-Active Particle Complexes and of Targeting Peptide-Active Particle Complexes Active particles are prepared from a polymer using a coacervation method. Preferably, particle size is between about 5 nm and 750 μm, more preferably between about 10 nm and 500 μm and most preferably between about 50 nm and 800 nm. MTLPs or targeting peptides are complexed to the particles using various methods known to those skilled in the art.

The following is a general method for preparation of coacervated particles.

Phase A

A polymer agent, a surface-active agent, a surface-stabilizing agent, a surface-modifying agent or a surfactant is dissolved in water (A). Preferably the agent is a polyvinyl alcohol (hereinafter "PVA") or a derivative thereof having a % hydrolysis of about 50-100 and a molecular weight range of about 500-500,000 kDa. More preferably the agent is a PVA having a % hydrolysis of 80-100 and a molecular weight range of about 10,000-150,000 kDa. The mixture (A) is stirred under low shear conditions at 10-2000 rpm and, more preferably, at 100-600 rpm. The pH and ionic strength of the solution may be modified using salts, buffers or other modifying agents. The viscosity of the solution may be modified using polymers, salts, or other viscosity modifying agents.

Phase A may include agents such as, but not limited to, emulsifying agents, detergents, solubilizing agents, wetting agents, foaming agents, antifoaming agents, flocculents and defloculents. Examples include, but are not limited to, anionic surface agents such as sodium dodecanoate, sodium dodecyl-(lauryl)sulphate, sodium dioctyl-sulphosuccinate, cetostearyl alcohol, stearic acid and its salts such as magnesium stearate and sodium stearate, sodium dodecyl-benzene sulphonate, sodium cholate triethanolamine; cationic surface agents such as hexadecyl trimethyl ammonium bromide (cetrimide), dodecyl pyridinium iodide, dodecyl pyridinium chloride; non-ionic surface agents such as hexaoxyethylene monohexadecyl ether, polysorbates (Tweens), sorbitan esters (Spans), Macrogol ethers, Poloxalkols (Poloxamers), PVA, PVP, glycols and glycerol esters, fatty alcohol poly glycol ethers, dextrans, higher fatty alcohols; and, amphoteric surface agents such as N-dodecyl alanine, lecithin, proteins, peptides, polysaccharides, semisynthetic polysaccharides, sterol-containing substances, and finely divided solids such as magnesium hydroxide and montmorillonite clays.

Phase B

A polymer is dissolved in a water miscible organic solvent to form the organic phase (B). Preferably the organic phase is an acetone-ethanol mixture in ratios from 0:100 acetone: ethanol to 100:0 acetone:ethanol depending upon the polymer used. Other polymers, peptides, sugars, salts, natural-polymers, synthetic polymers or other agents may be added to the organic phase (B) to modify the physical and chemical properties of the resultant particle product.

The polymers may be soluble, permeable, impermeable, biodegradable or gastroretentive. They may be a mixture of natural or synthetic polymers and copolymers. Such polymers include, but are not limited to, polylactides, polyglycolides, DL, L and D forms of poly(lactide-coglycolides) (PLGA), copolyoxalates, polycaprolactone, polyesteramides, polyorthoesters, polyanhydrides, polyalkylcyanoacrylates, polyhydroxy-butyrates, polyurethanes, albumin, casein, citosan derivatives, gelatin, acacia, celluloses, polysaccharides, alginic acid, polypeptides and the like, copolymers thereof, mixtures thereof, enantiomeric forms thereof, stereoisomers thereof and any MTLP conjugate thereof. Synthetic polymers include, but are not limited to, alkyl celluloses, hydroxyalkyl celluloses, cellulose ethers; cellulose esters, nitrocelluloses, acrylic and methacrylic acids and esters thereof, dextrans, polyamides, polycarbonates, polyalkylenes, polyalkylene glycols, polyalkylene oxides, polyalkylene terephthalates, polyvinyl alcohols, polyvinyl ethers, polyvinyl esters, polyvinyl halides, polyvinylpyrrolidones, polysiloxanes, polyurethanes and copolymers thereof.

Phase C

Phase B is stirred into phase A at a continuous rate. Solvent is evaporated, preferably by increasing the temperature over ambient and/or by using a vacuum pump. The resultant particles are in the form of a suspension (C)

An active agent may be added into phase A or into phase B. Active agent loading may be in the range 0-90% w/w. An MTLP or a targeting peptide may be added into phase C. MTLP and targeting peptide loading may be in the range 0-90% w/w.

Phase D

The particles (D) are separated from the suspension (C) using standard colloidal separation techniques including, but not limited to, centrifugation at high ‘g’ force, filtration, gel permeation chromatography, affinity chromatography or charge separation. The liquid phase is discarded and the particles (D) are re-suspended in a washing solution such as, but not limited to, water, salt solution, buffer or organic solvent. The particles are separated from the washing liquid using standard colloidal separation techniques and are washed two or more times. A MTLP or targeting peptide may be used to wash the particles or, alternatively, may be dissolved in the final wash. The particles are dried.

A secondary layer of polymers, peptides sugars, salts, natural and/or biological polymers or other agents may be deposited onto the preformed particulate core by any suitable method known in the art. The dried particles can be further processed by, for example, tableting, encapsulating or spray drying. The release profile of the particles formed may be varied from immediate to controlled or delayed release depending on the formulation used and/or desired.

EXAMPLE 3

Bovine Insulin Loaded-MTLP Coated Nanoparticles—MTLP Added in the Final Wash

Fast acting bovine insulin (28.1 IU/mg) was incorporated into polylactide-co-glycolide (PLGA, Boehringer Ingelheim, Indianapolis, Ind.) at a theoretical loading of 300 IU of insulin/210 mg of nanoparticles and the nanoparticles were coated with the dansylated ZElan094 (SEQ ID NO: 48).

| COMPONENT | AMMOUNT |
|---|---|
| PLGA RG504H (Lot # 250583) | 2 g |
| Acetone | 45 mls |
| Ethanol | 5 mls |
| PVA (5% w/v) (13-23 kDa, 98% hydrolysis) | 400 mls |
| Bovine Insulin (Lot # 86HO674) | 100 mg |
| ZElan094 (SEQ. ID NO: 48) | 10 mg/50 ml dH20 |

Preparation:

1. Water was heated to near boiling, PVA was added to 5% w/v and the solution was stirred until cool (phase A).
2. Acetone and ethanol were mixed to form the organic phase (phase B).
3. PLGA was added to the acetone and ethanol (step 2) and dissolved by stirring (phase B).
4. An IKA™ reactor vessel was set at 25° C. Phase A (step 1) was added into the reactor vessel and stirred at 400 rpm.
5. Bovine insulin was added into the stirring phase A (step 4).
6. Using clean tubing and a green needle, phase B (step 3) was slowly dripped into the stirring solution (step 5) using a peristaltic pump set at 40.
7. The solvent was evaporated by opening the IKA™ reactor vessel ports and stirring overnight at 400 rpm to form a suspension (phase C).
8. The suspension, phase C (step 7) was centrifuged in a XL90 centrifuge at 12,500 to 15,000 rpm for 25 to 40 minutes at 4° C.
9. The supernatant was discarded, the particle “cake” broken up, and the particles (phase D) washed twice in 200 ml of $dH_20$ by centrifugation in an XL90 centrifuge at 12,500 to 15,000 rpm for 10-15 minutes at 4° C. The dansylated ZElan094 (SEQ ID NO: 48) was added into the final wash.
10. The supernatant was decanted, the ‘cake’ broken up and the particles dried in a vacuum oven. The dried particles were ground, placed in a securitainer and analyzed.

Insulin loading was 5% or 50 mg insulin/g particles. Insulin potency, determined in HPLC, was 51.4 mg/g. Scanning electron microscopy showed discrete, reasonably spherical particles of about 300-400 nm in diameter.

EXAMPLE 4

Bovine Insulin Loaded-MTLP Coated Nanoparticles—MTLP Added to Phase C

Fast acting bovine insulin (28.1 IU/mg) was incorporated into PLGA nanoparticles at a theoretical loading of 300 IU of insulin/210 mg of nanoparticles and the nanoparticles were coated with the MTLP ZElan094 (SEQ ID NO: 48).

| COMPONENT | AMOUNT |
|---|---|
| PLGA RG504H (Lot # 250583) | 2 g |
| Acetone | 45 mls |
| Ethanol | 5 mls |
| PVA (5% w/v) (13-15 kDa, 98% hydrolysis) | 400 mls |
| Bovine Insulin (Lot #. 86HO674) | 100 mg |
| ZElan094 (SEQ. ID NO: 48) | 10 mg/50 ml dH20 |

Preparation:

See steps 1-4 of Example 3.

Step 5. Insulin and ZElan094 were added to the stirring PVA solution.

See steps 6-9 of Example 3.

The particles (step 9) were ground, placed in a securitainer and anlayzed.

EXAMPLE 5

Bovine Insulin Loaded-MTLP Coated Nanoparticles—MTLP Added 1 Hour Prior to Centrifugation Fast acting bovine insulin (28.1 IU/mg) was incorporated into PLGA nanoparticles at a theoretical loading of 300 IU of insulin/210 mg of nanoparticles and the nanoparticles were coated with dansylated ZElan094 (SEQ ID NO: 48).

| COMPONENT | AMOUNT |
|---|---|
| PLGA RG504H (Lot # 250583) | 2 g |
| Acetone | 45 mls |
| Ethanol | 5 mls |
| PVA (5% w/v) (13-15 kDa, 98% hydrolysis) | 400 mls |
| Bovine Insulin (Lot #. 86HO674) | 100 mg |
| ZElan094 (SEQ. ID NO: 48) | 10 mg/50 ml dH20 |

Preparation.

See steps 1-7 of Example 3.

Step 8. ZElan094 was added to the stirring particle suspension. After 1 hr, the suspension was centrifuged at 12,500-14,000 rpm for 20 to 40 min at 4° C.

See steps 9-10 of Example 3.

EXAMPLE 6

Bovine Insulin Loaded-MTLP Nanoparticles—MTLP Conjugated Polymer

Fast acting bovine insulin is incorporated into PLGA-dansylated ZElan094 (SEQ ID NO: 48) conjugate nanoparticles at a theoretical loading of 300 IU of insulin/210 mg of nanoparticles as follows.

| COMPONENT |
|---|
| PLGA RG504H (Lot # 250583) |
| RG504H-ZElan094 (SEQ ID NO: 48) conjugate |
| Acetone |
| Ethanol |
| PVA (5% w/v) (13-15 kDa, 98% hydrolysis) |
| Bovine Insulin |

Preparation is as in steps 1-10 of Example 3, except that in step 3 RG504H and RG504H-ZElan094 conjugate are added to phase B (step 2).

EXAMPLE 7

Bovine Insulin Loaded-Target Peptide Coated Nanoparticles

Fast acting bovine insulin (28.1 IU/mg) was incorporated into PLGA nanoparticles at a theoretical loading of 300 IU of insulin/210 mg of nanoparticles and the nanoparticles were coated with the targeting peptides dansylated ZElan 011, 055, 091, 101, 104, 128, 129 and 144 (SEQ ID NOS: 49, 51, 50, 52, 56, 55, 54 and 53).

| COMPONENT | AMOUNT |
|---|---|
| PLGA RG504H (Lot # 250583) | 2 g |
| Acetone | 45 ml |
| Ethanol | 5 ml |
| PVA (5% w/v) (13-15 kDa, 98% hydrolysis) | 400 ml |
| Bovine Insulin (Lot #. 86HO674) | 100 mg |
| ZElan011, 055, 091, 101, 104, 128, 129 and 144 (SEQ ID Nos: 49, 51, 50, 52, 56, 55, 54 and 53) | 10 mg/50 ml dH20 |

Preparation:

See steps 1-10 of Example 3.

Insulin loading was 5% or 50 mg insulin/g particles.

EXAMPLE 8

Animal Studies

In vivo oral insulin bioavailability from MTLP-insulin particle complexes (Example 3) and from targeting peptide-insulin particle complexes (Example 7) were assessed in the open loop rat model.

Fifty-nine Wistar rats (300-350g) were fasted for 4 hours and were anaesthetized by intramuscular injection of 0.525 ml of ketamine (100 mg/ml)+0.875 ml of acepromazine maleate-BP (2 mg/ml) 15 to 20 minutes prior to administration of MTLP-insulin particle complexes or of targeting peptide-insulin particle complexes. The rats were divided into 9 groups, each group containing 6 or 7 animals. Approximately 200 mg of MTLP-insulin (300 IU) particle complexes, suspended in 1.5 ml of PBS, were injected intra-duodenally at 2-3 cm below the pyloris of each of 6 rats (Group 5). Approximately 200 mg of targeting peptide-insulin (300 IU) particle complexes, suspended in 1.5 ml of PBS, were injected intra-duodenally at 2-3 cm below the pyloris of each of 6-7 rats (Groups 1-4 and 6-9). The study groups are shown in Table 5.

TABLE 5

Study Groups

| GROUP # | # OF RATS | PEPTIDE | ZELAN NO | SEQ ID NO: |
|---|---|---|---|---|
| 1 | 6 | HAX42 | 091 | 50 |
| 2 | 7 | PAX2 | 144 | 53 |
| 3 | 7 | PAX2 | 129 | 54 |
| 4 | 6 | P31 | 101 | 52 |
| 5 | 6 | MTLP | 094 | 48 |
| 6 | 7 | PAX2 | 128 | 55 |
| 7 | 7 | PAX2 | 104 | 56 |
| 8 | 7 | HAX42 | 011 | 49 |
| 9 | 7 | PAX2 | 055 | 51 |

Systemic blood was sampled from the tail vein (0.4 ml) of each rat at 0 minutes and at 15, 30, 45, 60 and 120 minutes after intra-duodenal administration of the ZElan094-insulin particle complexes or of the targeting peptide-insulin particle complexes. Blood glucose in each sample was measured using a Glucometer (Bayer; 0.1 to 33.3 μm/mol/L). The blood was centrifuged and the plasma was retained. Plasma insulin was assayed in duplicate using a Phadeseph RIA Kit (Pharmacia, Piscataway, N.J.; 3 to 240 μU/ml).

Figure 2:
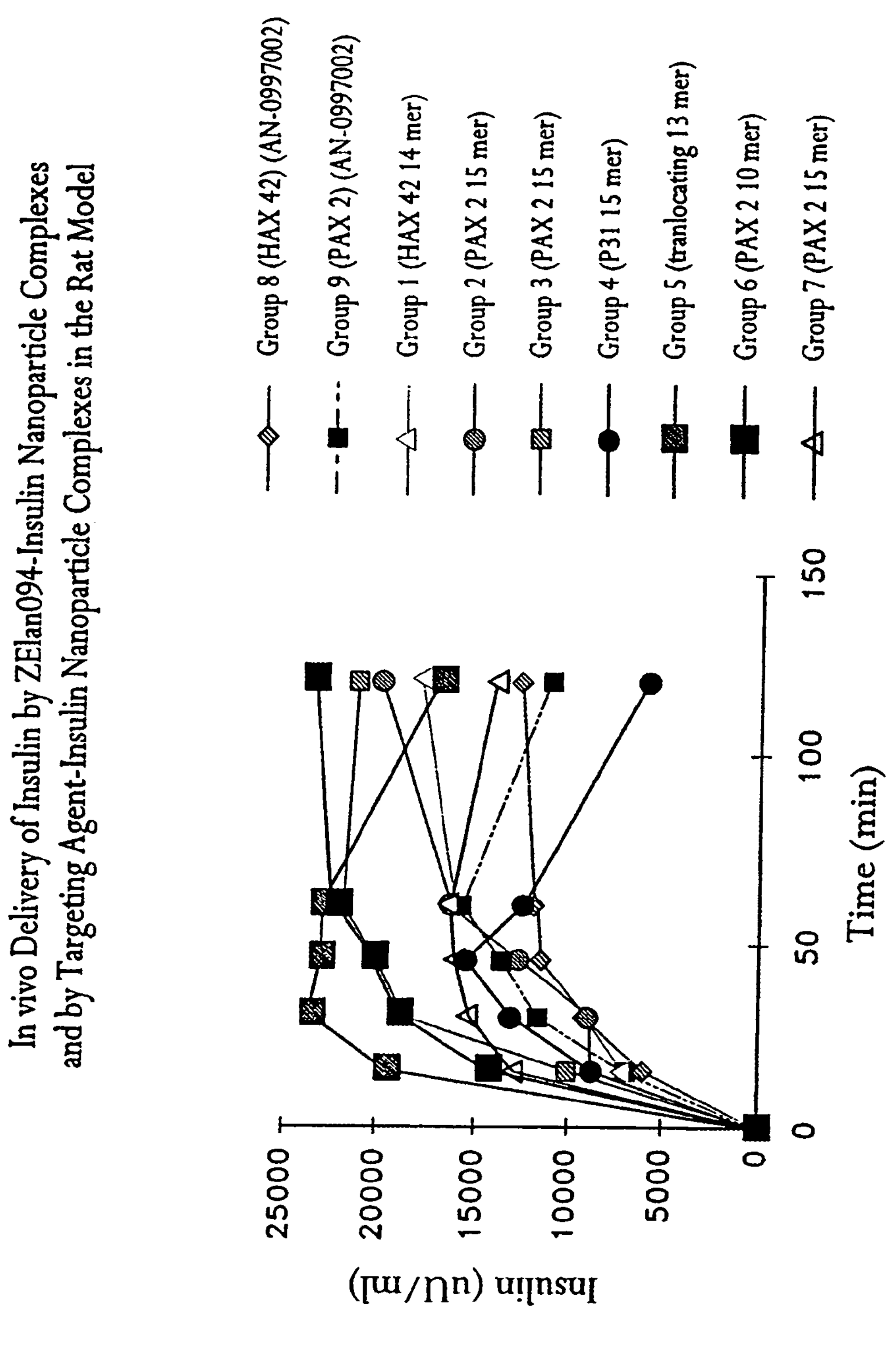
FIG. 2 shows the systemic blood insulin levels following in vivo delivery of insulin from a ZElan094-insulin nanoparticle complex and from HAX42-, PAX2- and P31-insulin nanoparticle complexes in the open loop rat model. Each point is the mean of from 6-7 animals.

FIG. 2 shows the plasma insulin levels following intra-duodenal administration of ZElan094-insulin particle complexes (Group 5) and of targeting peptide ZElan091- (Group 1), 144- (Group 2), 129- (Group 3), 101- (Group 4), 128- (Group 6), 104- (Group 7) and 011-(Group 8) insulin particle complexes. As shown in FIG. 2, during the 60 minutes following intra-duodenal administration, ZElan094-insulin particle complexes provided the most potent enhancement of insulin delivery followed by ZElan055-, 129- and 094-, 101-, 128-, 091- and 144, and 011-insulin particle complexes. These data show that the plasma insulin levels obtained using MTLP-insulin particle complexes, were greater than those obtained using the targeting peptide-insulin particle complexes.

Figure 3:
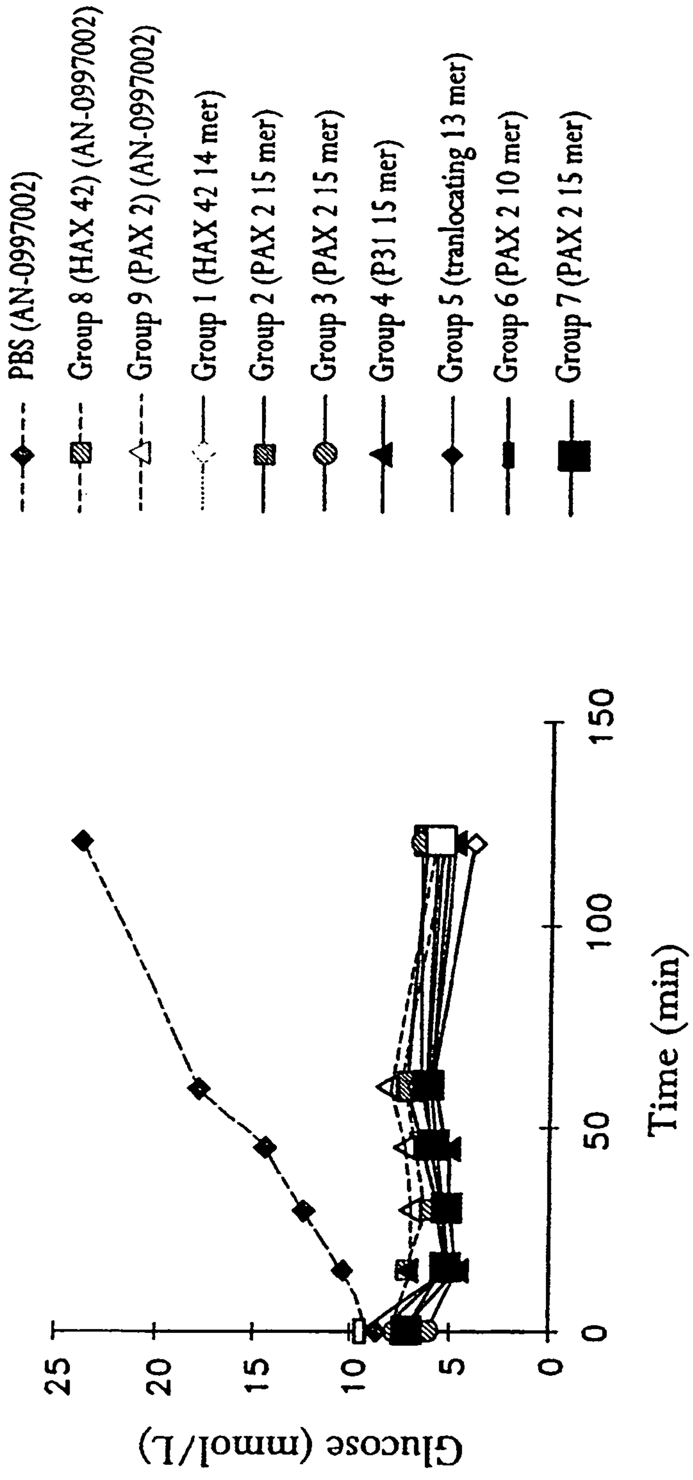
FIG. 3 shows the systemic blood glucose levels following in vivo delivery of insulin from a ZElan094-insulin nanoparticle complex and from HAX42-, PAX2- and P31-insulin nanoparticle complexes in the open loop rat model. Each point is the mean of from 6-7 animals.

To ensure that the insulin delivered from the MTLP-insulin particle complexes and from the targeting peptide-insulin particle complexes was bioactive, blood glucose levels were measured. As shown in FIG. 3, during the 20 minutes following intra-duodenal administration, blood glucose levels fell from between about 6.0-9.5 mmol/L to about 4.5-7.0 mmol/L and remained significantly below control values (PBS) for at least 60 minutes. There was no significant differences in blood glucose levels among the animals receiving the MTLP-insulin particle complexes and the animals receiving the targeting peptide-insulin particle complexes at 60 minutes and at 120 minutes. These data show that insulin delivered from the dansylated ZElan094-insulin particle complexes and from the dansylated Zelan011, 055, 091, 144, 129, 101, 129, 128 and 104-insulin particle complexes remained bioactive. Further, these data show that insulin delivered from MTLP-insulin particle complexes enabled a significant and long lasting decrease in blood glucose levels.

EXAMPLE 9

Preparation of DNA Containing Liposomes and of DNA Containing MTLP Coated Liposomes DNA containing liposomes and DNA containing MLTP coated liposomes were prepared as follows:

Solution 1 Twelve nmol lipofectamine (Gibco BRL, Rockville, Md.),±0.6 μg of protamine sulphate, was prepared in a final volume of 75 μl optiMEM.

Solution 2 One μg of pHM6lacZ DNA (Boehringer Mannheim) was prepared in a final volume of 75 μl optiMEM. The reporter plasmid pHM6lacZ contains the lacZ gene, which codes for bacterial β-galactosidase.

Solution 3 Solution 1 and Solution 2 were combined and incubated for 15 minutes at RT to enable complex formation.

Solution 4 ZElan094, 204N or 204 (SEQ ID Nos: 2, 23, 24) were added to Solution 3 to a final concentration of 100 μM and incubated for 5 minutes at RT. Six-hundred μl of optiMEM was added and the solution was mixed gently.

The DNA containing liposomes and the DNA containing MTLP coated liposome complexes were analyzed in scanning electron microscopy (SCM) or in transmission electron microscopy (TEM) to confirm complex liposome formation and by zeta potential analysis to confirm surface charge properties.

EXAMPLE 10

Delivery of DNA from Liposomes and from MTLP-Liposomes into Caco-2 Cells

DNA delivery into Caco-2 cells from liposomes and from MTLP coated liposomes was calculated as β-galactosidase expression per μg of total protein in the cell supernatant. β-galactosidase expression was determined using the Boehringer Mannheim chemiluminescence kit. Protein was determined using the Pierce Micro bichinconate (BCA) protein assay.

Caco-2 cells were plated at $1\times10^5$ cells/well in 1 ml of culture media and incubated at 37° C. in 5% $CO_2$ overnight. The cells were washed twice in 0.5 ml of optiMEM. ZElan094, 204N or 204 (SEQ ID NOS: 2, 23, 24) (Solution 4, Example 9) were each added to triplicate wells (250 μl/well) of the washed cells and incubated for 4 h at 37° C. After 4 h, 250 μl of optiMEM containing 2× fetal calf serum was added and the cells were incubated for an additional 20 h at 37° C. At 24 h post-transfection, the cells were lysed with Boehringer Mannheim Lysis Buffer. The lysate was centrifuged for 2 min at 14,000 rpm in an Eppendorf Centrifiguge and the supernatant was collected.

Table 6 shows relative β-galactosidase expression per μg of total protein using ZElan094, ZElan204N and ZElan204 (SEQ ID NOS: 2, 2324) coated liposomes as the DNA delivery particles.

TABLE 6

β-galactosidase expression in Caco-2 cells

| | EXPERIMENTS | |
|---|---|---|
| | 1 | 2 |
| Lipofectamine + DNA (control) | 100% | 100% |
| Lipofectamine + DNA + protamine (control) | 90% | 162% |
| Lipofectamine + DNA + protamine + ZElan094 | 387% | 260% |
| Lipofectamine + DNA + protamine + ZElan204N | 495% | 217% |
| Lipofectamine + DNA + protamine + ZelanN204 | 176% | 122% |

The MLTPs ZElan094, 204N and N204 (SEQ ID NOS: 2, 23 and 24) coated liposomes delivered more DNA into the Caco-2 cells than did the lipofectamine+DNA and lipofectamine+DNA+protamine control liposomes. Moreover, as indicated by β-galactosidase expression, the ZElan094 derivative ZElan204N, which is modified at the C-terminus by the addition of a nuclear localisation sequence (NLS), was most effective in enhancing both delivery of DNA into and expression of DNA within Caco-2 cells. The MTLP ZElan094 and its derivatives, in combination with cationic lipids and DNA condensing agents, enhanced both the targeting of genes to cells and the subsequent uptake of the genes by the cells.

As MTLPs enhance uptake of both active-agents and active-particles into cells, MTLPs including, but not limited to, ZElan094 and ZElan 204N, can be used as coating agents on polymer based particle systems and on liposome based particle systems as active agent and active particle delivery systems. Further, MTLPs also can be used as coating agents on viral vector based particle systems including, but not limited to, adenovirus, adeno-associated virus, lentivirus, and vaccinia virus. In such systems, the virus itself may code for the MTLP, wherein the DNA sequence coding for the MTLP has been cloned in frame to one or more genes which code for one or more viral capsid protein or for one or more viral surface proteins. Alternatively, the surface of the virus used for gene delivery may be modified with a MTLP following virus production and purification from a cell including, but not limited to, a mammalian cell.

EXAMPLE 11

Effects of MTLPs and of the Targeting Peptides on Substrate Transport Across a Cell Layer The effect of the MTLPs ZElan094, ZElan178 and ZElan187 (SEQ ID NOS: 2, 58 and 59) and of the targeting peptide ZElan022 (SEQ ID NOS: 57) on the transport of the dipeptide $^{14}$C-gly-sar and of the reporter molecule $^{3}$H-fMLP across Caco-2 monolayers was determined. The Caco-2 monolayers were grown on Transwell-Snapwells. Cell viability was determined by measuring TEER of the Caco-2 monolayers during each experiment. No significant drop in TEER was measured. Cell permeability was determined by measuring mannitol flux across the Caco-2 monolayers during each experiment. No increase in mannitol flux was measured in the presence of the MTLP ZElan094.

The flux of the dipeptide $^{14}$C-gly-sar and of the reporter molecule $^{3}$H-fMLP across the Caco-2 monolayers in the absence and in the presence of the MTLPs ZElan094, ZElan178 and ZElan187 (SEQ ID NOS: 2, 58 and 59) and of the targeting peptide ZElan022 (SEQ ID NO: 57) was measured over 2 h, and reduction in the permeability coefficient was determined in the presence of cold substrates.

Figure 4:
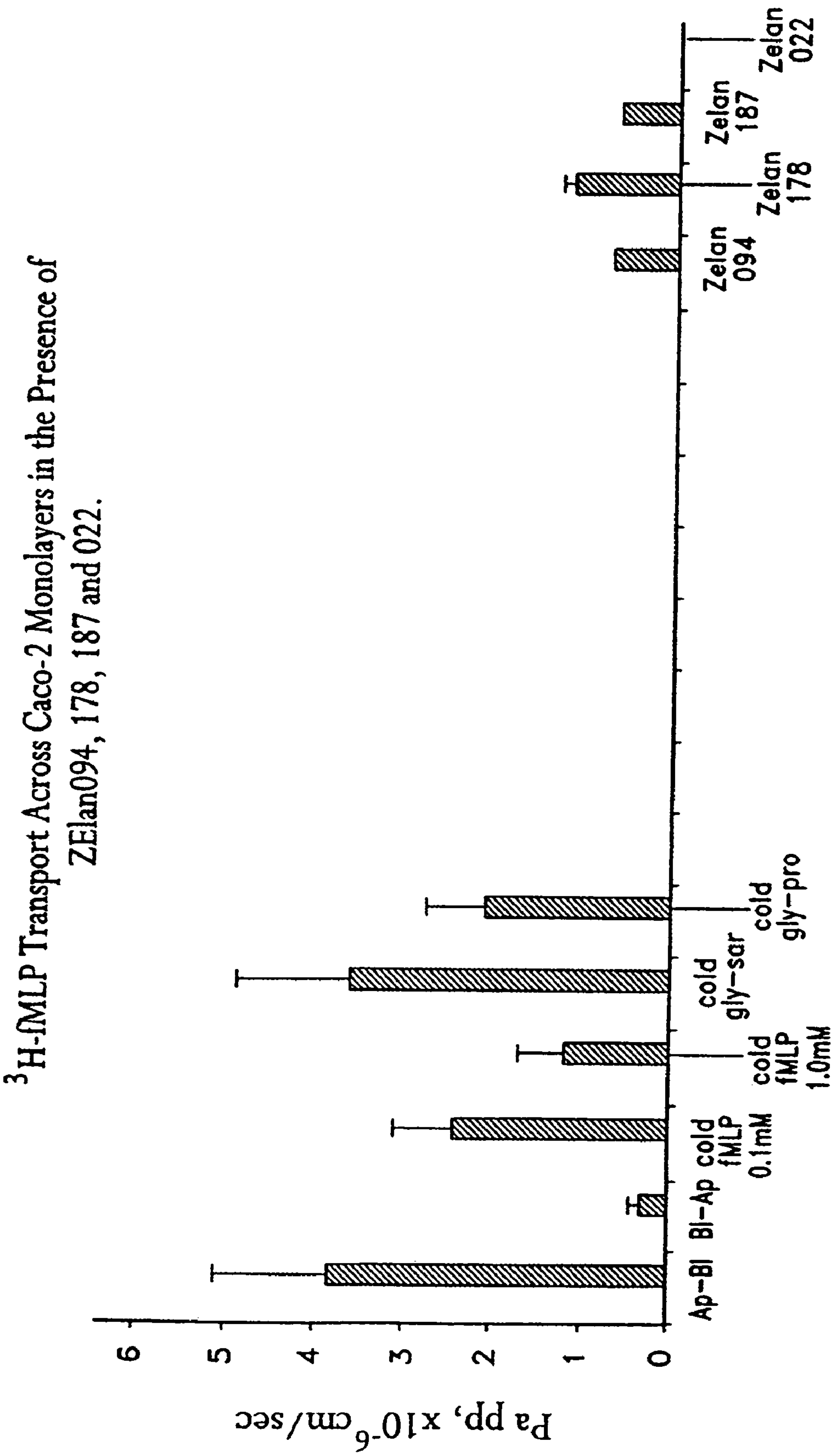
FIG. 4 shows the transport of the reporter drug $^3$H-fMLP across Caco-2 monolayers in the presence of the MTLPs Zelan094, 178, 187 and the targeting peptide ZElan022.

As shown in Table 7, the MTLPs ZElan 094, 178 and 187 inhibited transport of the reporter molecule $^{3}$H-fMLP (FIG. 4), but did not inhibit transport of the dipeptide $^{14}$C-gly-sar. The targeting peptide ZElan 022 inhibited transport of the reporter molecule $^{3}$H-fMLP (FIG. 4). The ability of the MTLPs ZElan094, 178 and 187 to compete for the transport of fMLP across polarised Caco-2 cells indicates that this novel transport assay can be used to screen derivatives, fragments, motifs, analogs and peptidomimetics of ZElan094 and small organic molecules functionally similar to ZElan094 to identify those having improved transport characteristics.

TABLE 7

Transport studies

| ZElan N0: | SEQ ID NO: | % inhibition $^{3}$H-fMLP transport | % inhibition $^{14}$C-gly-sar transport |
|---|---|---|---|
| 094 | 2 (15 mer) | 77.2 | NS |
| 178 | 58 (10mer cyclic) | 71.5 | NS |

TABLE 7-continued

Transport studies

| ZElan N0: | SEQ ID NO: | % inhibition $^{3}$H-fMLP transport | % inhibition $^{14}$C-gly-sar transport |
|---|---|---|---|
| 187 | 59 (10mer | 84.5 | NS |
| 022 | 59 (10mer) | 00.0 | |

NS: no significant difference between experimental (+MTLP) and control cells (−MTLP) in the transport of radiolabeled drug.

Moreover, that the MTLPs inhibited transport of the reporter molecule $^{3}$H-fMLP, but did not inhibit transport of the dipeptide $^{14}$C-gly-sar suggest that their effect on fMLP transport is not due to a generalized perturbation of the membranes in polarized epithelial cells. Further, as fMLP is known to play a role in inflammation in the GIT, MTLPs, which decrease transport of fMLP across Caco-2 monolayers, may have a therapeutic role in preventing local inflammation by decreasing the chemoattractant effect of fMLP in the GIT.

EXAMPLE 12

Figure 5:
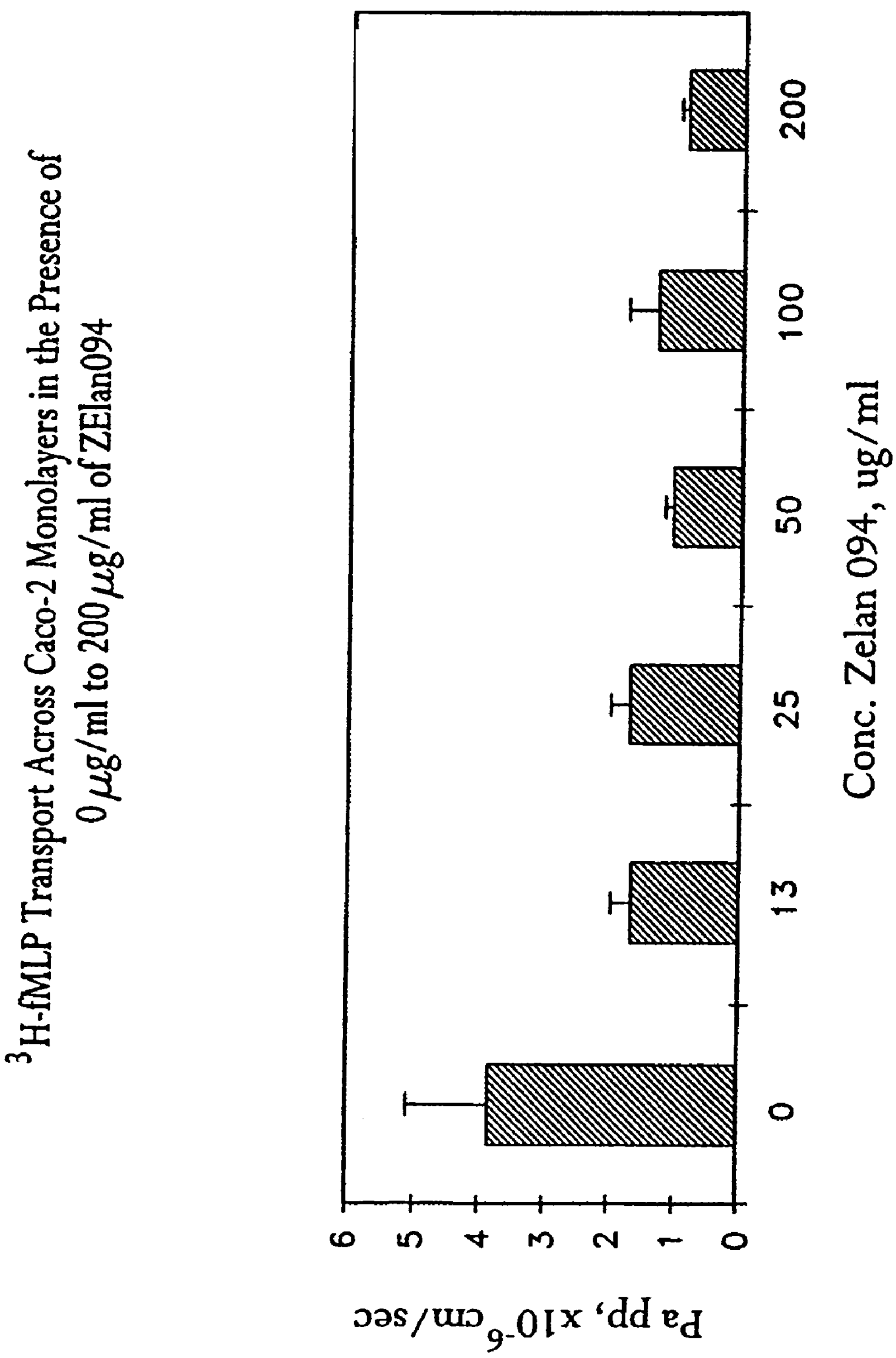
FIG. 5 shows the transport of the reporter drug $^3$H-fMLP across Caco-2 monolayers in the presence of increasing concentrations of the MTLP ZElan094.

Effect of Increasing Concentrations of an MTLP on the Transport of $^{3}$H-fMLP Across a Cell Layer Caco-2 monolayers were grown and tested for viability as in Example 11. Transport of $^{3}$H-fMLP across Caco-2 monolyers was measured in the presence from 0 to 200 μg/ml of the MTLP ZElan094. As shown in FIG. 5, the MTLP ZElan094 inhibited $^{3}$H-fMLP transport even at the lowest concentration (13 μg/ml or 7.1 μl) tested. This indicates that the MTLP ZElan094 is a potent inhibitor of fMLP transport across an epithelial cell layer.

The present invention is not to be limited in scope by the specific embodiments described herein. Various modifications of the invention in addition to those described herein will become apparent to those skilled in the art from the foregoing description and accompanying figures. Such modifications are intended to fall within the scope of the appended claims.

We claim:

1. A composition comprising a peptide having the amino acid sequence as set forth in SEQ ID NO: 24 and a carrier.

2. The composition of claim 1, further comprising an active agent, selected from the group consisting of therapeutic agent, prophylactic agent, and diagnostic agent, wherein said peptide is complexed to said active agent.

3. A composition according to claim 2, wherein said active agent comprising DNA is complexed with a membrane translocating peptide (MTLP)-coated liposome.

4. The composition of claim 1, further comprising an active particle, selected from the group consisting of nanoparticle, liposome, and microparticle, wherein said peptide is complexed to said active particle.

5. A composition for use in membrane translocation, the composition consisting of the MTLP comprising an amino acid sequence of SEQ ID NO: 24 and a carrier.

6. A composition of claim 5, wherein said MTLP is complexed to a liposome.

7. A pharmaceutical composition comprising the composition according to claim 1 and a pharmaceutical carrier.

8. A pharmaceutical composition according to claim 7, adapted for oral administration.

9. A pharmaceutical composition comprising a composition according to claim 5 and a pharmaceutical carrier.

10. A pharmaceutical composition according to claim 6, adapted for oral administration.

11. A method for enhancing movement of an active agent selected from the group consisting of therapeutic agent, prophylactic agent, and diagnostic agent, across a lipid membrane, comprising a administering the composition of claim 2 to said membrane wherein the peptide enhances movement of the active agent across the lipid membrane.

12. A method for enhancing movement of an active particle selected from the group consisting of nanoparticle, liposome, and microparticle, across a lipid membrane, comprising a administering the composition of claim 4 to said membrane wherein the peptide enhances movement of the active particle across the lipid membrane.

13. A method for treating a pathological disorder in an animal, comprising orally administering to the animal in need of such treatment the composition of claim 8 wherein an amount of the active agent effective to treat the pathological disorder is moved across the gastrointestinal epithelium of the animal into the circulation.

* * * * *